(12) United States Patent
Coln et al.

(10) Patent No.: US 11,293,891 B2
(45) Date of Patent: Apr. 5, 2022

(54) METHODS AND SYSTEMS FOR READOUT OF NANOGAP SENSORS

(71) Applicant: Analog Devices International Unlimited Company, Limerick (IE)

(72) Inventors: Michael Coln, Lexington, MA (US); Mark Daniel de Leon Alea, Metro Manila (PH)

(73) Assignee: Analog Devices International Unlimited Company, Limerick (IE)

( * ) Notice: Subject to any disclaimer, the term of this patent is extended or adjusted under 35 U.S.C. 154(b) by 323 days.

(21) Appl. No.: 16/143,897

(22) Filed: Sep. 27, 2018

(65) Prior Publication Data

US 2019/0113476 A1    Apr. 18, 2019

Related U.S. Application Data

(60) Provisional application No. 62/572,649, filed on Oct. 16, 2017.

(51) Int. Cl.
*G01N 27/327*    (2006.01)
*G01N 33/487*    (2006.01)
(Continued)

(52) U.S. Cl.
CPC ......... *G01N 27/3278* (2013.01); *G01N 27/00* (2013.01); *G01N 27/4145* (2013.01);
(Continued)

(58) Field of Classification Search
None
See application file for complete search history.

(56) References Cited

U.S. PATENT DOCUMENTS

| 6,437,553 B1* | 8/2002 | Maloney | G01R 31/3016 324/617 |
| 2002/0043998 A1* | 4/2002 | Misdom | H03K 17/063 327/205 |

(Continued)

OTHER PUBLICATIONS

Laifi et al., High Resolution Current-Mode CCO-Based Continuous Time Delta-Sigma Modulators for Sensor-Array Applications, 978-1-4799-499-6/14, 2014, IEEE, 4 pages. (Year: 2014).*

(Continued)

*Primary Examiner* — Matthew D Krcha
(74) *Attorney, Agent, or Firm* — Patent Capital Group

(57) ABSTRACT

Embodiments of the present disclosure relate to various methods and example systems for carrying out analog-to-digital conversion of data acquired by arrays of nanogap sensors. The nanogap sensors described herein may operate as molecular sensors to help identify chemical species through electrical measurements using at least a pair of electrodes separated by a nanogap. In general, the methods and systems proposed herein rely on digitizing the signal as the signal is being integrated, and then integrating the digitized results. With such methods, the higher sample rate used in the digitizer reduces the charge per quantization and, therefore, the size of sampling capacitors used. Consequently, sampling capacitors may be made factors of magnitude smaller, requiring less valuable space on a chip compared to sampling capacitors used in conventional nanogap sensor arrays.

20 Claims, 16 Drawing Sheets

(51) Int. Cl.
*G01N 27/00* (2006.01)
*H03K 3/03* (2006.01)
*G01N 27/414* (2006.01)
*G01N 33/497* (2006.01)
*H03K 3/0231* (2006.01)
*H03M 1/60* (2006.01)
*B82Y 15/00* (2011.01)

(52) U.S. Cl.
CPC ..... *G01N 33/48721* (2013.01); *G01N 33/497* (2013.01); *H03K 3/0322* (2013.01); *B82Y 15/00* (2013.01); *H03K 3/0231* (2013.01); *H03K 3/0315* (2013.01); *H03M 1/60* (2013.01)

(56) References Cited

U.S. PATENT DOCUMENTS

| | | | | |
|---|---|---|---|---|
| 2005/0057388 | A1* | 3/2005 | Terazawa | G04F 10/005 341/157 |
| 2008/0037008 | A1* | 2/2008 | Shepard | G01N 21/6408 356/73 |
| 2008/0258953 | A1* | 10/2008 | Farley | H03M 1/64 341/144 |
| 2010/0194945 | A1 | 8/2010 | Chiu et al. | |
| 2010/0267158 | A1* | 10/2010 | Chou | C12Q 1/68 436/94 |
| 2013/0063166 | A1* | 3/2013 | Ng | H03K 3/0231 324/682 |

OTHER PUBLICATIONS

Ghoreishizadeh, *Integrated Electronics to Control and Readout Electrochemical Biosensors for Implantable Applications*, Jun. 1, 2015, Ecole Polytechnique Federal de Lausanne, Suisse, 193 pages.

Cardes et al., *SNDR Limits of Oscillator-Based Sensor Readout Circuits*, Sensors 2018, 18, 445; doi: 10.3390/s18020445, Published Feb. 3, 2018, www.mpdi.com/journal/sensors, 16 pages.

Laifi et al., *High Resolution Current-Mode CCO-Based Continuous Time Delta-Sigma Modulators for Sensor-Array Applications*, 978-1-4799-499-6/14 © 2014 IEEE, 4 pages.

Eder et al., *A CMOS Smart Temperature and Humidity Sensor with Combined Readout*, Sensors 2014, 14, 17192-17211; doi: 10.3390/s140917192, www.mdpi.com/journal/sensors, 20 pages.

Laifi et al., *CCO-Based Continuous-Time ΔΣ Modulators for Electrochemical Sensor Arrays*, MIXDES 2014, 21$^{st}$ International Conference Mixed Design of Integrated Circuits and Systems, Jun. 19-21, 2014, Lublin, Poland, 6 pages.

Choudhuri et al., *Study of Voltage-Controlled Oscillator Based Analog-to-Digital Converter*, Thesis, National Institute of Technology, Rourkela, 2011, 49 pages.

Haile et al., *Oscillator Circuits for RTD Temperature Sensors*, AN895, Microchip, © 2004 Microchip Technology, Inc., 28 pages.

Alipour, *Investigation of Biosensor for DNA Detection*, Thesis, Massy University, School of Engineering and Advanced Technology (SEAT), Auckland, New Zealand, Jan. 2011, 112 pages.

Sun et al., *A Low Power Low Supply Sensitivity Current-Mode Relaxation Oscillator*, IEICE Electronics Express, vol. * No. *,*-*, © IEICE 2014, 6 pages.

* cited by examiner

METHODS AND SYSTEMS FOR READOUT OF NANOGAP SENSORS

CROSS-REFERENCE TO RELATED APPLICATIONS

This application claims the benefit of and priority from U.S. Provisional Patent Application Ser. No. 62/572,649 filed 16 Oct. 2017, entitled "METHODS AND SYSTEMS FOR READOUT OF NANOGAP SENSORS", incorporated herein by reference in its entirety.

TECHNICAL FIELD OF THE DISCLOSURE

The present invention relates to the field of sensors, in particular to sensors for evaluating analytes based on electron tunneling through a nanometric-sized gap between at least a pair of electrodes, and to methods and systems for readout of such sensors.

BACKGROUND

Evaluation of molecular content of various analytes is important in applications across a large variety of fields. For example, molecular identification may be used in deoxyribonucleic acid (DNA) or ribonucleic acid (RNA) sequencing used in biological research. In another example, identification of various gasses (e.g., $CO_2$, CO, $CH_4$, $H_2S$, etc.) or liquids (e.g., water) may be needed as some gasses or liquids may be dangerous for the environment or the living beings, as well as detrimental to the functionality or/and the efficiency of various devices such as e.g., integrated circuit (IC) chips.

Nanogap sensors may be used for evaluating molecular content of analytes.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

Figure 1:
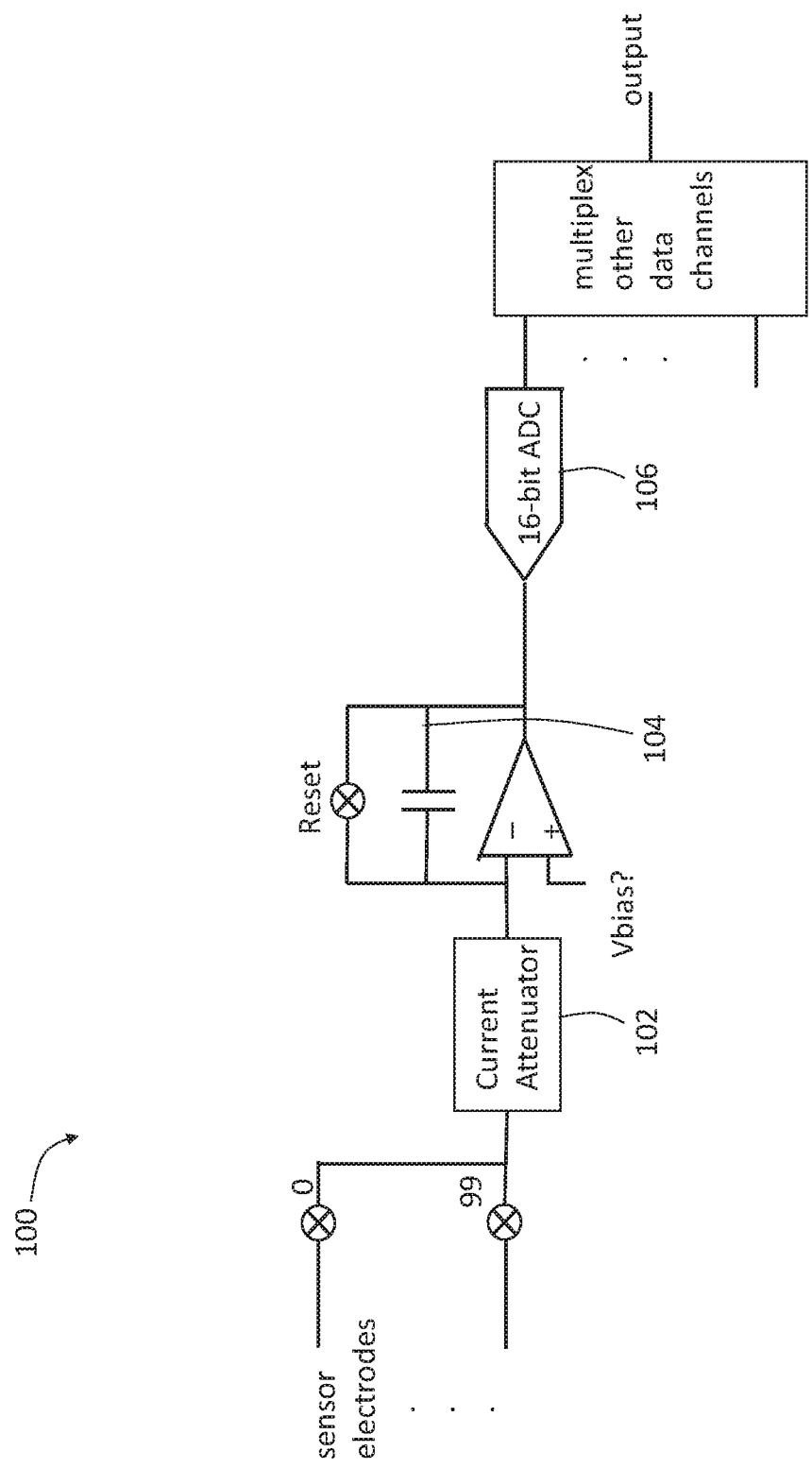
FIG. 1 illustrates a conventional nanogap sensor readout system.

As described above, nanogap sensors may be used for evaluating molecular content of analytes. In general, the term "nanogap sensor" refers to a device where at least two electrodes are separated by a nanometric-sized, tightly-confined region of space (i.e., a nanogap, also referred to as a "query volume") in which an analyte (i.e., a substance whose chemical constituents are being identified and/or measured) is provided. When voltage is applied to one or more of the electrodes, electrons can travel from a first electrode to a second electrode by tunneling. The molecules of the analyte present inside the nanogap affect electron tunneling. Therefore, readout of the current through the nanogap allows identification and evaluation of the molecular species within the nanogap.

Throughput and accuracy of nanogap sensors may be improved by parallel operation of millions of sensors on a given chip. However, implementing such large numbers of nanogap sensors is not an easy task. In particular, challenges arise when analog data acquired by the nanogap sensors is converted to a digital signal using an analog-to-digital converter (ADC), as explained below.

In conventional implementations of ADCs used in nanogap sensor systems, an input signal, which may be a current signal from an array of nanogap sensors (e.g., 100 nanogap sensors), is sampled onto a capacitor or an array of capacitors commonly referred to as "integration capacitors" or "sampling capacitors," prior to digitization (also referred to as "quantization") taking place, i.e., prior to generating a digital value or sequence of digital values representative of the charge integrated (i.e., accumulated) on the sampling capacitor(s). During the sampling operation, charge is accumulated onto the sampling capacitor(s) from a circuit driving the sampling capacitor(s) (i.e., the nanogap sensor in this case) so that the sampling capacitor(s) are charged to a voltage corresponding to the value of the input signal at that time. Terms such as "acquisition/acquire phase" or "sampling phase" may be used to describe a phase, i.e., a time period, when sampling capacitor(s) connected to an input node at which the input signal is received are being charged to a voltage corresponding to the input signal. In other words, "acquire phase" or "sampling phase" refer to a time period when sampling capacitor(s) are integrating an analog input signal in preparation for converting the analog input signal to a digital output signal. Terms "sampling" and "acquire phase" may be used interchangeably to refer to the action of one or more sampling capacitors connected to an input node integrating or sampling an input signal during a certain time period. An acquire phase is followed by a phase that is typically referred to as a "conversion phase," where charge representative of an analog value of the input signal accumulated on the sampling capacitor(s) is converted, by circuits sometimes referred to as "quantizers," to a digital value by comparison of the charge accumulated on the sampling capacitor(s) with one or more reference voltage values. After acquisition and conversion phases for converting one analog input value are finished, processing described above is repeated for the next analog input value.

Problems with the above-described ADCs arise in context of nanogap sensors because full scale currents generated by the sensors are relatively large, which requires large sampling capacitors used for the analog-to-digital conversion of the currents. Trying to implement sufficient number of such large sampling capacitors results in unacceptably high demand on surface area of a chip because the larger the capacitance of a capacitor, the larger is the area occupied by the capacitor.

Conventional techniques to address this issue rely on attenuating the current before integrating it on a sampling capacitor. One channel of such a conventional system is shown as a system 100 in FIG. 1 where a current attenuator 102 is used to attenuate current provided by a single channel comprising an array of a plurality of nanogap sensors (shown in FIG. 1 as "sensor electrodes" 0-99) prior to integrating the current on a sampling capacitor 104, where the result of the integration of each measurement is then provided to an ADC 106 for digitizing.

In order to get the sampling capacitors to a sufficiently small size, current may have to be attenuated as much as by a factor of $10^4$, i.e., the level of attenuation is extreme. Therefore, approaches that could improve in digitizing analog data acquired by nanogap sensors would be desirable.

Embodiments of the present disclosure are based on recognition that approaches to converting analog currents generated by nanogap sensors to their digital representation in ways that could eliminate, or at least reduce, the need for current attenuation while eliminating the need for prohibitively large sampling capacitors would be desirable, where the nanogap sensors described herein may operate as molecular sensors to help identify chemical species through electrical measurements using at least a pair of electrodes separated by a nanogap. To that end, various approaches for converting analog currents generated by nanogap sensors to their digital representation are proposed, the various approaches being explained in terms of methods and example systems, in particular, example nanogap sensor arrangements, for carrying out said methods. In general, the various approaches proposed herein are based on recognition that a conventional approach of, first, integrating the entire analog signal for a given measurement, and only afterwards digitizing with a high-dynamic-range ADC is the root of the problem because integrating the entire signal for a given measurement, which takes about 1 second in time, requires having very large sampling capacitors which would be capable of holding all of the charge integrated. Instead, the methods proposed herein rely on digitizing the signal already as the signal is being sampled, as then integrating the digitized results. In other words, methods proposed herein are based on digitizing the signal with a higher bandwidth (which involves only a short-term integration of a portion of a signal), and then integrating (i.e., accumulating) the digitized results. With such methods, the higher sample rate used in the digitizer reduces the duration of each conversion, reducing the charge per quantization and, therefore, the size of any sampling capacitors used. Consequently, the sampling capacitors may be made factors of magnitude smaller, requiring less valuable space on a chip compared to sampling capacitors used in conventional nanogap sensor arrays and being small enough for circuits of millions of nanogap sensors to be manufacturable and commercially viable. Furthermore, accumulation of the digitized results may advantageously involve a digital counter, which size grows only logarithmically with the length of the overall measurement time. An additional benefit is that the digital decimation (i.e., averaging) may effectively improve the signal-to-noise of the digitizer, so a lower resolution (i.e., noisier) quantizer may suffice, thus relaxing the demands on the quantizer performance.

As used herein, description of any of the nanogap sensors with reference to measuring chemical content of a target analyte assumes that, unless specified otherwise, a sensor can merely detect presence or absence of the target analyte, or may assess/evaluate/quantify the amount of the target analyte or various molecular components therein. Furthermore, while some nanogap sensors described herein may be described with reference to specific chemical(s) being an example target analyte of interest (such as e.g., DNA), these sensors are by no means limited to detecting presence and/or amount of such chemicals, and can easily be extended to measurements of other target analytes. In some implementations, the nanogap sensors described herein may be used for molecular measurements in a liquid phase (i.e., the analyte provided in the nanogap may be liquid), e.g., as used in DNA/RNA sequencing, reading of epigenetic markers, protein detection and identification, and various applications not related to life science, such as e.g., industrial chemical measurement. In other implementations, the nanogap sensors described herein may be used for molecular measurements in a gaseous phase (i.e., the analyte provided in the nanogap may be gaseous), e.g., as used in gas sensors or in identification and quantification of chemical species in vehicles or buildings. Thus, the nanogap sensors described herein may be used for molecular measurements where analytes are provided in a fluid form.

As will be appreciated by one skilled in the art, aspects of the present disclosure, in particular aspects of analog-todigital conversion of data acquired by nanogap sensors proposed herein, may be embodied in various manners—e.g., as systems used to carry out measurement of target analytes, methods used to fabricate said systems as well as methods used to operate said systems, computer program products comprising computer-readable instructions which, when executed on a processor, can operate said systems, or computer-readable storage media, preferably non-transitory, used to store such computer-readable instructions. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Some functions described in this disclosure may be implemented as algorithms executed by one or more processing units, e.g., one or more microprocessors, of one or more computers.

Other features and advantages of the disclosure will be apparent from the following description, and from the select examples.

The following detailed description of various embodiments of the present disclosure is organized as follows. First, basics of DNA sequencing is described, followed by a description of an example system, shown in FIG. 2, used for analog-to-digital conversion of data acquired by nanogap sensors. After that, four proposed alternatives for analog-to-digital conversion of data acquired by nanogap sensors to be implemented within such a system, as well as their variations and implementations, are described with reference to various nanogap sensor arrangements as shown in FIGS. 3-16.

Basics of DNA Sequencing

In some implementations, systems with nanogap sensor arrays proposed herein may be used for DNA sequencing. In general, DNA sequencing may be performed by applying an electrical field to the DNA strand provided in a nanogap of a nanogap sensor, where the field is applied using electrodes of the nanogap sensor, and measuring the resulting tunneling current through the nanogap. Different base pairs will deliver different tunneling current characteristics (both current amplitude and time characteristics), which allows differentiation between these pairs.

An alternative approach to DNA sequencing may include attaching base pair labels biochemically and performing biochemistry on large arrays of nanogap sensors substantially simultaneously. Such an approach may be beneficial because it may provide an easier manner for discriminating between base pairs due to label selectivity and may advantageously result in various tunneling currents across the nanogaps that are easier to distinguish from one another.

While DNA sequencing techniques have been rapidly advancing in recent years, there are still challenges to overcome, such as e.g., processing very large numbers of base reads in parallel, discriminating between pairs, getting reproducible reads from a given strand independent of the sensor variations, performing measurements sufficiently quickly, and dealing with read errors. In particular, improvements in obtaining digital data from the nanogap sensor arrays are needed.

Example Nanogap Sensor System

Figure 2:
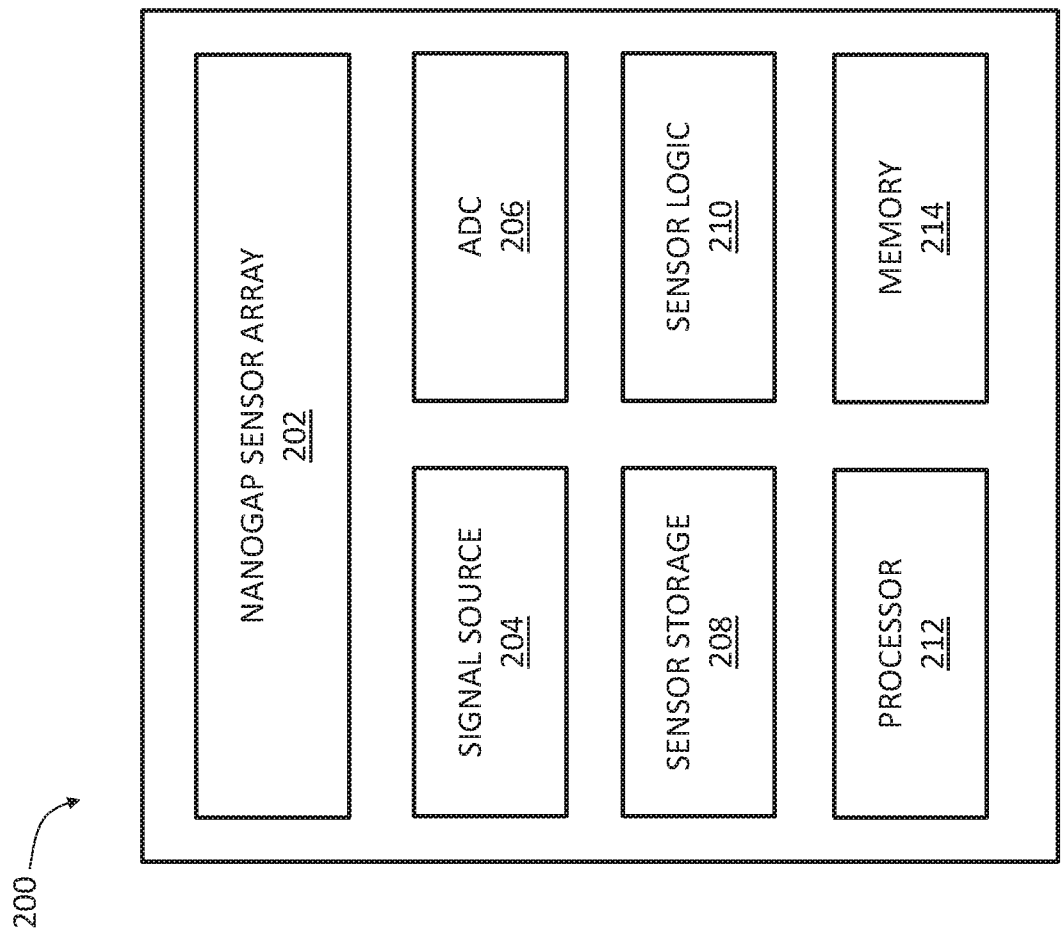
FIG. 2 illustrates an example nanogap sensor system configured to implement analog-to-digital conversion of data acquired by nanogap sensors in accordance with various embodiments of the present disclosure.

FIG. 2 illustrates an example nanogap sensor system 200, according to some embodiments of the present disclosure. As shown in FIG. 2, the example system 200 may include an array of nanogap sensors 202, where sensors may be grouped into channels, e.g., 100 nanogap sensors per channel, and may be arranged on a chip or a substrate in any suitable geometry, e.g., arranged in rows and columns, or arranged in any other configuration that may be optimal in terms of fabrication, operation, and/or readout. Oftentimes, including multiple nanogap sensors in the array 202, e.g., hundreds, thousands, or even millions of nanogap sensors, may be desirable as it may improve throughput and accuracy by parallel operation of multiple sensors on a given chip.

As briefly described above, each nanogap sensor includes at least a pair of electrodes, facing one another and separated by a nanogap, to which signals are applied in order to evaluate the chemical species in the nanogap. In some embodiments, the nanogap between the pair of electrodes may be between about 1 and 100 nanometers, including all values and ranges therein, e.g. between about 2 and 50 nanometers, or between about 5 and 20 nanometers, and may be oriented either substantially horizontally (i.e., with the electrodes of the pair being substantially parallel to the substrate on which the nanogap sensor is provided) or substantially vertically (i.e., with the electrodes of the pair being substantially perpendicular to the substrate on which the nanogap sensor is provided). In some embodiments, one or more layers of specifically designed molecules may be provided on at least portions of surfaces of either one or both of the pair of electrodes that face one another. Such layers may promote attachment of analytes to be evaluated, which may be advantageous for certain tests to be carried out using the nanogap sensor system. In some embodiments, such one or more layers may be self-assembled monolayer (SAMs), and may include one or more of thiols (R—S—H), di-thiols (H—S—R—S—H), or alkanethiols (e.g., mercapto-propanol, mercaptohexanol, dithiols).

In some embodiments, using more than two electrode for a given query volume (i.e., for what may be considered a single nanogap sensor) may be beneficial as it may allow for more measurements of current tunneled through the query volume and may highlight more detailed characteristics of the species in the query volume, e.g., different pairs of electrodes may be used to query the volume along various spatial directions. Hence, unless stated otherwise, for each of the nanogap sensors described herein, even though two electrodes may be described (each pair of electrodes illustrated in FIGS. with a single line labeled "sensor electrode"), the descriptions may be extended to more than two electrodes, all of which descriptions being within the scope of the present disclosure. Furthermore, some of the electrodes of multiple sensors may be shared, as long as each nanogap sensor has a unique combination of a first and a second electrode (i.e., as long as each nanogap sensor of an array has at least a first electrode or a second electrode that is different from corresponding electrodes of all other nanogap sensors).

As shown in FIG. 2, the nanogap sensor system 200 may include a signal source 204 for applying appropriate signals to the electrodes of the nanogap sensors in the array 202. The signal source 204 may be configured to apply various signal waveforms to each electrode pair as "query waveforms."

As further shown in FIG. 2, the nanogap sensor system 200 may also include one or more ADCs 206. As used herein, the term "ADC" refers to an electronic circuit/device that converts a continuous physical quantity carried by an analog signal to a digital number that represents the quantity's amplitude (or to a digital signal carrying that digital number). The result is a sequence of digital values (i.e., a digital signal) that has converted a continuous-time and continuous-amplitude analog input signal to a discrete-time and discrete-amplitude digital signal. In case of the ADC 206 used in the nanogap sensor system 200, the analog input signal being converted may be signal indicative of the electrical current across the nanogap(s) of the one or more nanogap sensors of the nanogap sensor array 202. The ADC 206 may be implemented according to any of the alternative designs proposed herein, which can be chosen based on the operating characteristics required by different applications. Thus, although shown separately in FIG. 2, the ADC 206 may be implemented together, i.e., integrated with, the nanogap sensor array 202. For example, the relaxation oscillators together with counters described herein may serve as one or more ADCs 206 of FIG. 2, implemented together with the one or more nanogap sensors 202.

Turning back to FIG. 2, the sensor readings corresponding to (i.e., indicative of) currents through the nanogaps of the one or more nanogap sensors in the array 202 may be stored in a sensor storage 208, which may be any suitable array of memory elements. In some embodiments, the sensor storage 208 may include an array of capacitors, where voltage on each capacitor is indicative of the current though a nanogap of a particular nanogap sensor or a collection of nanogap sensors in a channel, possibly for a particular arrangement of a pair of electrodes around such a gap (e.g., in case multiple pairs of electrodes are used for a single nanogap). The sensor storage 208 may be considered as a part of the ADC 206. In some embodiments, the sensor storage 208 may include an array of registers storing digital values of counters coupled to the relaxation oscillators described herein and configured to store count values of the counters, which count values represent oscillation frequencies of the relaxation oscillators and, thus, represent currents generated by various nanogap sensors of the nanogap sensor array 202, as described in greater detail below.

As also shown in FIG. 2, the nanogap sensor system 200 may further include nanogap sensor logic 210, which may be implemented in hardware, software, firmware, or any suitable combination of the one or more of these, is configured to control the operation of the analog-to-digital conversion of signals acquired by nanogap sensors of the nanogap sensor array 202 as described herein. To that end, the nanogap sensor logic 210 may make use of at least one processor 212 and at least one memory element 214, along with any other suitable hardware and/or software to enable its intended functionality of nanogap sensor readings in a nanogap sensor system as described herein. In some embodiments, the processor 212 can execute software or an algorithm to perform the activities as discussed in the present disclosure, e.g., the processor 212 can execute the algorithms that control analog-to-digital conversion of signals acquired by nanogap sensors of the nanogap sensor array 202 as well as the algorithms that carry evaluation of input analog values to measure the chemical species present within the nanogaps of the one or more nanogap sensors of the array 202 as described herein. Although shown as separate elements in FIG. 2, the processor 212 and/or the memory 214 may be considered to be a part of the nanogap sensor logic 210.

The processor 212 may be configured to communicatively couple to other system elements via one or more interconnects or buses. Such a processor may include any combination of hardware, software, or firmware providing programmable logic, including by way of non-limiting example a microprocessor, a digital signal processor (DSP), a field-programmable gate array (FPGA), a programmable logic array (PLA), an application specific IC (ASIC), or a virtual machine processor. The processor 212 may be communicatively coupled to the memory element 214, for example in a direct-memory access (DMA) configuration. Such a memory element may include any suitable volatile or non-volatile memory technology, including double data rate (DDR) random access memory (RAM), synchronous RAM (SRAM), dynamic RAM (DRAM), flash, read-only memory (ROM), optical media, virtual memory regions, magnetic or tape memory, or any other suitable technology. Unless specified otherwise, any of the memory items discussed herein should be construed as being encompassed within the broad term "memory element." The information being tracked or sent to the one or more nanogap sensors of the nanogap sensor array 202, the signal source 204, the ADC 206, the sensor storage 208, the nanogap sensor logic 210, the processor 212, or the memory 214 could be provided in any database, register, control list, cache, or storage structure, all of which can be referenced at any suitable timeframe. Any such storage options may be included within the broad term "memory element" as used herein. Similarly, any of the potential processing elements, modules, and machines described herein should be construed as being encompassed within the broad term "processor." Each of the elements shown in FIG. 2, e.g., the nanogap sensor logic 210 and the ADC 206, can also include suitable interfaces for receiving, transmitting, and/or otherwise communicating data or information in a network environment.

In certain example implementations, mechanisms for analog-to-digital conversion of signals acquired by nanogap sensors of the nanogap sensor array 202 in order to evaluate molecular content of analytes based on electrical readings across nanogaps in the nanogap sensor arrays as outlined herein may be implemented by logic encoded in one or more tangible media, which may be inclusive of non-transitory media, e.g., embedded logic provided in an ASIC, in DSP instructions, software (potentially inclusive of object code and source code) to be executed by a processor, or other similar machine, etc. In some of these instances, memory elements, such as e.g., the memory 214 shown in FIG. 2, can store data or information used for the operations described herein. This includes the memory elements being able to store software, logic, code, or processor instructions that are executed to carry out the activities described herein. A processor can execute any type of instructions associated with the data or information to achieve the operations detailed herein. In one example, the processors, such as e.g., the processor 212 shown in FIG. 2, could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., an FPGA, a DSP, an erasable programmable read-only memory (EPROM), an electrically erasable programmable read-only memory (EEPROM)) or an ASIC that includes digital logic, software, code, electronic instructions, or any suitable combination thereof.

Proposed Approach #1: Charge-Balancing Converter

Figure 3:
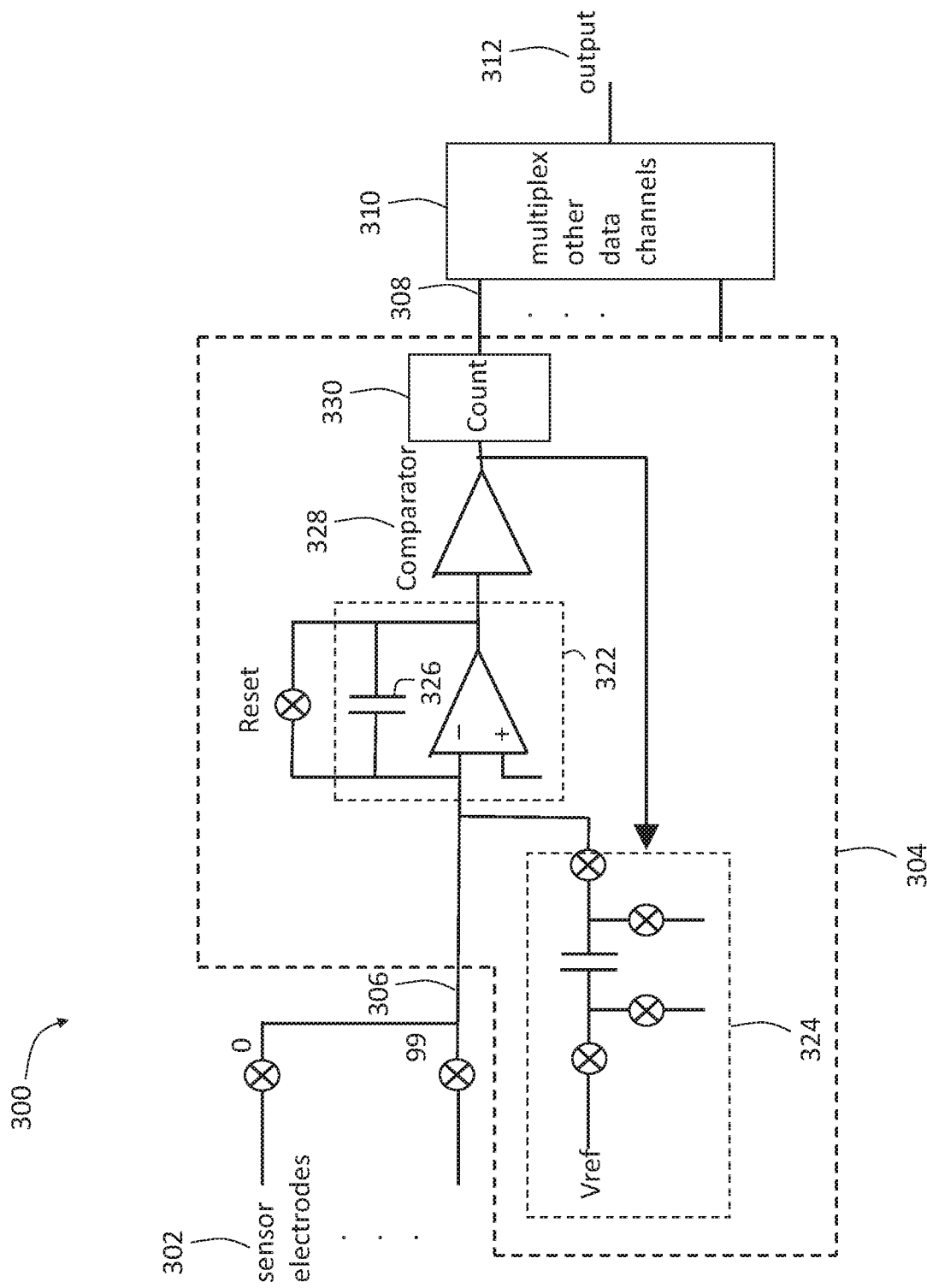
FIG. 3 provides a schematic illustration of a system for implementing a first proposed approach for analog-to-digital conversion of data acquired by nanogap sensors, in accordance with some embodiments of the present disclosure.

FIG. 3 provides a schematic illustration of a system 300 for implementing a first proposed approach for analog-to-digital conversion of data acquired by nanogap sensors, in accordance with some embodiments of the present disclosure.

As shown in FIG. 3, the system 300 includes an array of nanogap sensors 302, implementing one channel of the array 202 shown in FIG. 2. The nanogap sensors 302 are shown in FIG. 3 as 100 sensor electrodes 0-99, but, of course, in other embodiments any number of one or more nanogap sensors may be included/used as a channel of the array 202, all of which embodiments being within the scope of the present disclosure. As used herein, the term "channel" of an array of nanogap sensors refers to the circuitry that is time-multiplexed across an ensemble of sensors, such that the electrical signals from each of the sensors of a given channel are readout sequentially. Arranging multiple nanogap sensors in such channels may be advantageous from the perspective of efficiently using the channel area. Typically, sampling/quantization of an input signal generated by a given nanogap sensor (as used herein, the term "input signal" refers to an input to the sampling/quantization circuits where analog-to-digital conversion is performed, from the perspective of a nanogap sensor it is an output signal, i.e., a signal output from the nanogap sensor) takes much less time than the time needed for the biochemical measurement of the nanogap sensor (e.g., in some implementations, the former time may be about 1 second, while the latter can be about 100 seconds). Therefore, the readout circuitry performing the analog-to-digital conversion can be re-used many times to sequentially convert input signals generated by different nanogap sensors of a given channel, i.e., the outputs of the different nanogap sensors of a given channel can be multiplexed to sequentially convert the input signals generated by each of the sensors. While an example embodiment of such multiplexing is only shown in FIG. 10 of the present disclosure showing the nanogap sensors 1008 and the multiplex transistors 1010 used to implement "select" lines to select an output of which one of the nanogap sensors is being converted, such an example implementation of multiplexing between different nanogap sensors of a given channel is applicable to all other embodiments discussed herein.

As also shown in FIG. 3, the system 300 further includes a circuit 304 for implementing analog-to-digital conversion of an analog current 306 generated by the array of nanogap sensors 302 according to the proposed approach #1 described herein. As a result of the conversion, the circuit 304 outputs a digital signal 308. The digital signal 308 is for a given channel of the nanogap sensor array 302, and could be combined, e.g., using a multiplexer 310, with digital signals produced by other channels, to provide a total digital output 312. Nanogap sensor arrays of other channels, as well as their associated conversion circuitry, are not specifically shown in FIG. 3. However, it is within the scope of the present disclosure that such additional channels may be present, where arrays of nanogap sensor electrodes within each channel would be analogous to the nanogap sensor array 302 described above, and where, in various embodiments, the different channels may have ADC conversion circuitry similar to that shown with the circuit 304 associated with each channel individually, or shared among two or more channels.

The circuit 304 may be seen as a delta-sigma ADC implementing high-frequency quantization, followed by digital decimation (averaging or filtering). The circuit 304 may be configured to integrate continuously, e.g., using as an integrator the circuit 322 shown in FIG. 3, but periodically remove quanta of charge as necessary to limit voltage swing, which can e.g., be done using a cancellation circuit 324 as shown in FIG. 3.

If sampling interval used in the circuit 304 is selected to be much faster than measurement interval, the size of the integration capacitor 326 (which could be an array of capacitors) may be reduced proportionally. For example, the sigma-delta converter circuit 304 with a sampling rate of $10^5$ samples/second (s) may allow the capacitor 326 to be reduced to 10 femtoFarad (fF), significantly reducing chip area occupied by the capacitor 326.

The output 308 (# of feedback quanta) of the circuit 304 is then already in digital form, advantageously ready for decimation.

Furthermore, such an approach is likely to exhibit excellent linearity and noise, which are important characteristics of an ADC.

A comparator 328 shown in FIG. 3 is configured to control the operation of cancellation circuit 324, so the average current delivered by the cancellation circuit becomes equal and opposite to the average input current from the sensor currently being measured, while a counter 330 shown in FIG. 3 is configured to accumulate the activity of the cancellation circuit. In this fashion, the digital count becomes proportional to the input signal, and the desired analog-to-digital conversion has been performed.

Proposed Approach #2: VCO-Like Converter

Figure 4:
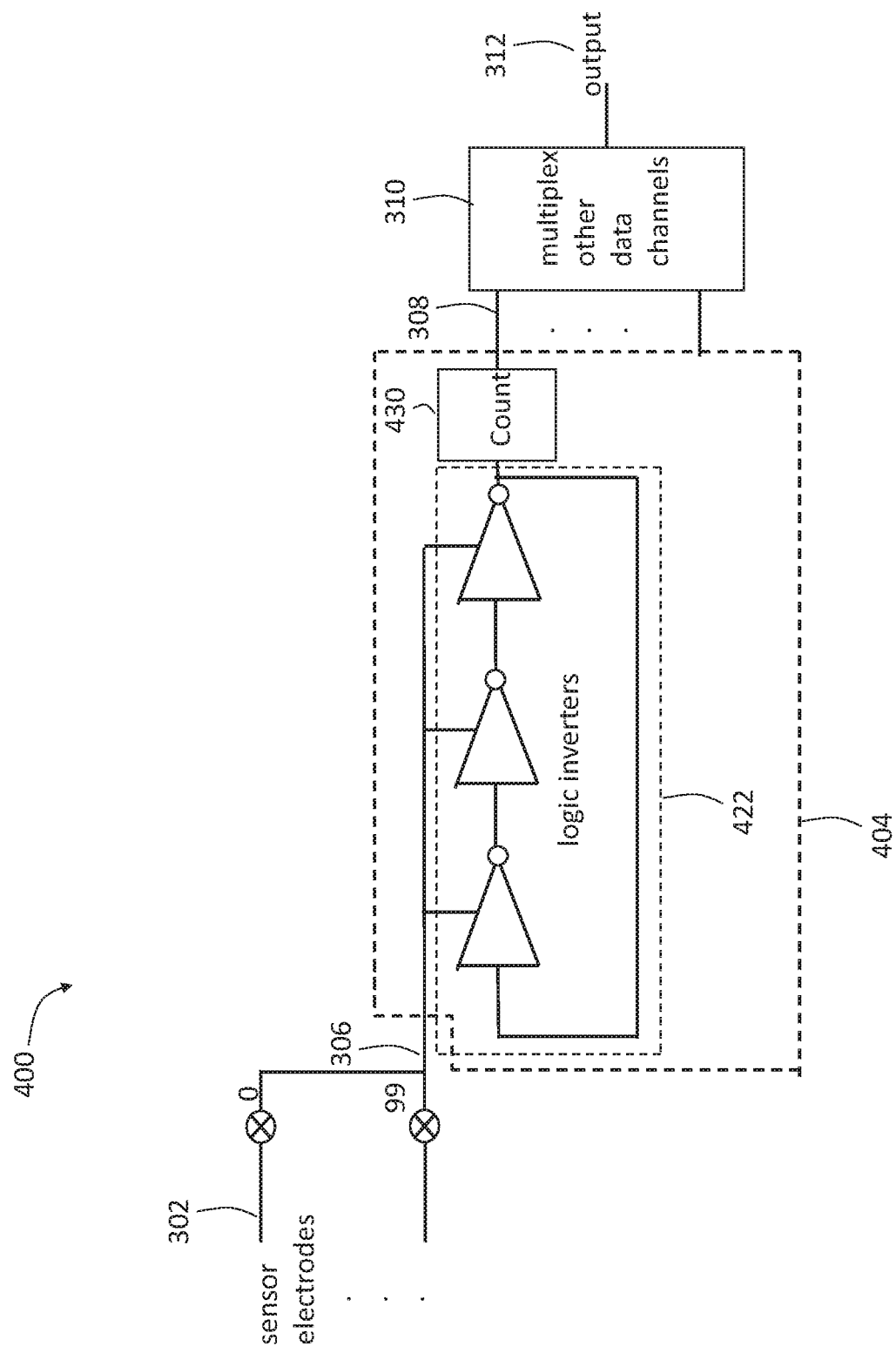
FIG. 4 provides a schematic illustration of a system for implementing a second proposed approach for analog-to-digital conversion of data acquired by nanogap sensors, in accordance with some embodiments of the present disclosure.

FIG. 4 provides a schematic illustration of a system for implementing a second proposed approach for analog-to-digital conversion of data acquired by nanogap sensors, in accordance with some embodiments of the present disclosure. FIG. 4 illustrates the array of nanogap sensors 302, the analog current 306, the digital signal 308, the multiplexer 310, and the final digital output 312 as shown in FIG. 3. Descriptions of those elements provided with respect to FIG. 3 are applicable to the system 400 shown in FIG. 4, and, therefore, in the interests of brevity, are not repeated. Instead, features specific to the approach #2 shown in FIG. 4 are described.

As shown in FIG. 4, the system 400 includes a circuit 404 for implementing analog-to-digital conversion of an analog current 306 generated by the array of nanogap sensors 302 according to the proposed approach #2 described herein. The circuit 404 may include a ring oscillator 422, controlled by the input current 306 generated by the nanogap sensor array 302. Current-controlled ring oscillators naturally transform an input current into an output frequency, and this functionality is exploited in the converter circuit 404 of FIG. 4.

The ring oscillator 422 is shown in the example of FIG. 4 as comprising 3 logic inverters. In other embodiments, any other number of logic inverters may be used. Such a ring oscillator would receive the analog signal 306 representative of the current from the nanogap sensors 302 as an input. The output of the ring resonator 422 would then oscillate between two voltage levels, with the ring oscillator frequency being proportional to the input signal 306. A counter 430 would then be able to derive the digital output 308 based on the frequency of the oscillations of the output of the ring oscillator 422.

The approach #2 an example implementation of which is illustrated in FIG. 4 may be considered as implementing a "VCO-like" quantizer in that the ring oscillator 422 is an electronic oscillator whose oscillation frequency is controlled by a current input (in a VCO, it would be controlled by a voltage input) where the applied input current determines the instantaneous oscillation frequency.

Using current as the input variable according to approach #2 may allow eliminating what is typically the biggest non-linearity, namely a trans-conductor circuit (often a simple resistor-degenerated transistor) used to transform an input signal voltage into the controlled current for the ring oscillator. Since the input signal is already in the current domain, no trans-conductor circuit is required, and so any artifacts from such a trans-conductor are avoided.

In some embodiments, the circuit 404 may further include a current mirror, in order to stabilize the signal input voltage (virtual ground).

Approach #2 as illustrated with an example of FIG. 4 has potential for implementing the circuit 404 using very small area, perhaps avoiding need for much multiplexing of multiple sensors into each readout circuit. Such an approach is also expected to scale well into finer lithographic nodes.

Proposed Approach #3: Converter Exploiting Transistor Gate Oxide Tunneling

Approach #3 may be considered as somewhat similar to the previous direct "VCO-like" converter. In general, approach #3 uses gate oxide tunneling in a transistor as a "pseudo-resistor" to convert sensor current to voltage. In particular, approach #3 includes applying the pseudo-resistor differential voltage to two relaxation oscillators, incorporating similar pseudo-resistors into oscillators to cancel non-linearities and sensitivities of pseudo-resistors, and producing a conversion result encoded in the frequency difference between oscillators.

Such an approach has a potential for very small area, and is expected to scale well into finer lithographic nodes. Furthermore, use of transistor "tunneling" currents may be especially well suited for digitizing very low currents, e.g., picoAmpere (pA) levels, produced by some nanogap sensors.

Figure 5:
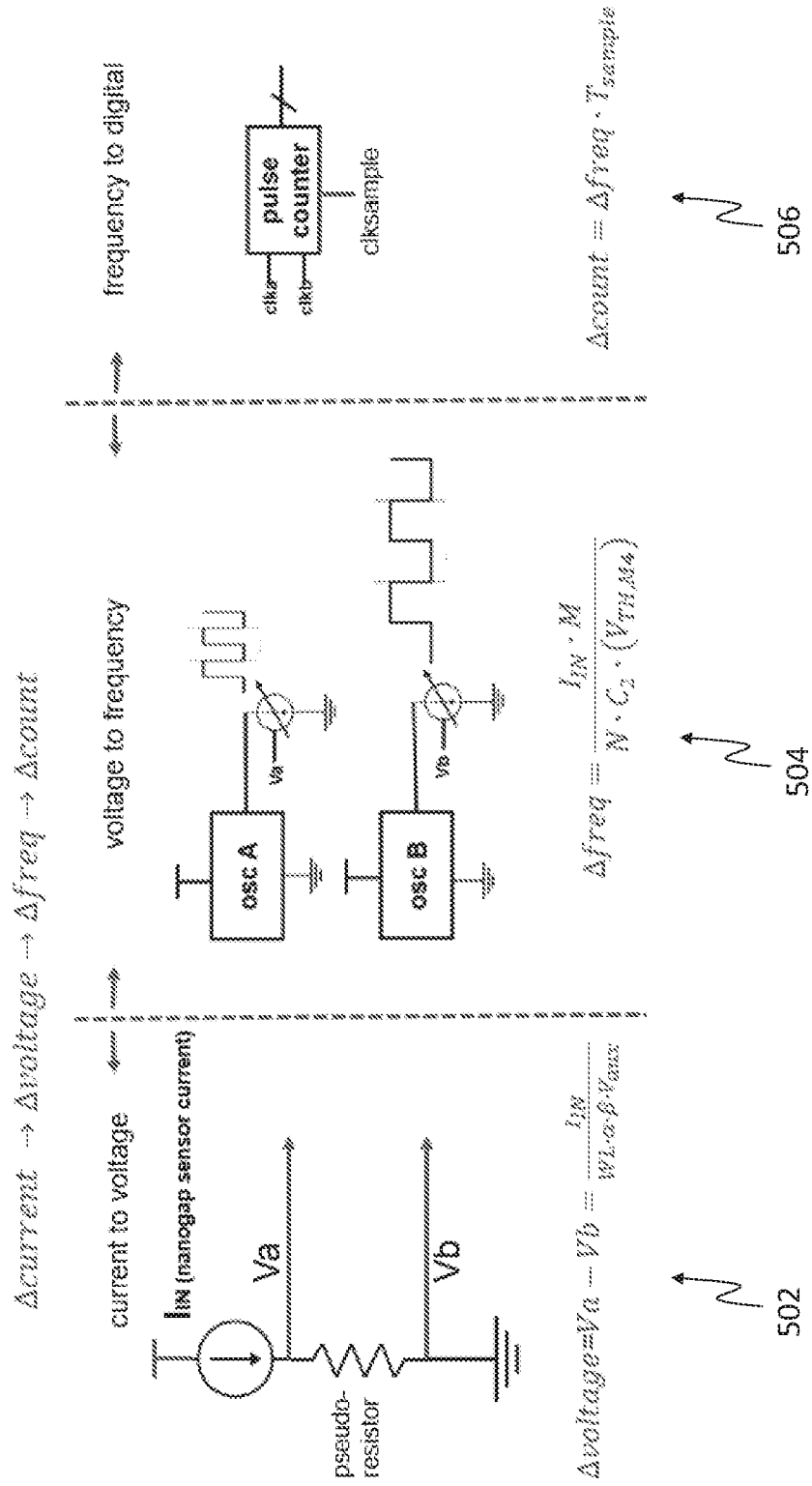
FIG. 5 provides a functional illustration of a third proposed approach for analog-to-digital conversion of data acquired by nanogap sensors, in accordance with some embodiments of the present disclosure.

FIG. 5 provides a functional illustration of approach #3, in accordance with some embodiments of the present disclosure. As illustrated in FIG. 5, approach #3 seeks to convert the sensor current signal $I_{IN}$ (e.g., current generated by each individual nanogap sensor of the nanogap sensor array 202), which is typically a very small current signal, into a digital measurement result by a sequence of transformations.

Figure 6:
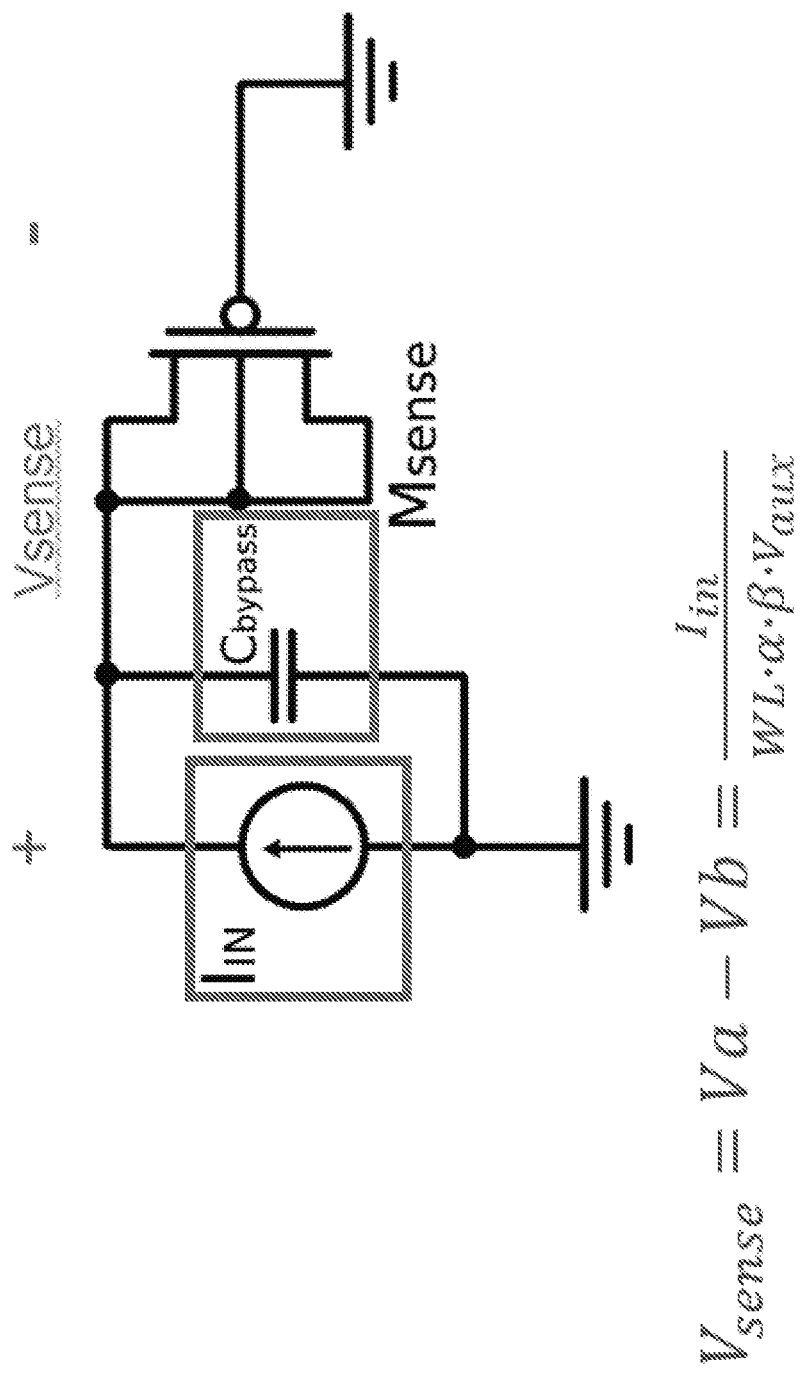
FIG. 6 provides a schematic illustration of a current to voltage conversion in the third proposed approach, in accordance with some embodiments of the present disclosure.

In a first transformation stage 502, which may be considered as a "current to voltage" transformation or conversion, the current $I_{IN}$ is passed through a pseudo-resistor, which pseudo-resistor may be implemented as the tunneling resistance through a metal-oxide-semiconductor (MOS) transistor as shown in FIG. 6. The voltage difference across the pseudo-resistor becomes the transformed signal. Va shown in FIG. 5 is the voltage on one side of the pseudo-resistor, while Vb shown in FIG. 5 is the voltage on the other side. A relation between the input current $I_{IN}$ and the voltage difference Va-Vb, which voltage difference is referred to as "Vsense" in the following, is shown in FIG. 5 with a formula provided at the bottom of the first transformation stage 502.

In a second transformation stage 504, which may be considered as a "voltage to frequency" transformation or conversion, two voltage-controlled-oscillators, shown in FIG. 5 as "osc A" and "osc B," are used to separately measure voltages Va and Vb on the pseudo-resistor of the first stage 502. Each oscillator may produce a frequency related to its input voltage, so the difference in frequency between the two oscillator outputs reflects the voltage difference across the pseudo-resistor of the first transformation stage 502, which, in turn, represents the sensor signal current $I_{IN}$. A relation between the input current $I_{IN}$ and the frequency difference is shown in FIG. 5 with a formula provided at the bottom of the second transformation stage 504.

In a third transformation stage 506, which may be considered as a "frequency to digital" transformation or conversion, the two frequencies are accumulated by a digital counter, shown in FIG. 5 as a "pulse counter," and so the difference count finally reflects the original sensor signal current $I_{IN}$. In this manner, input current is encoded as change in frequency. A relation between the frequency difference and count difference is shown in FIG. 5 with a formula provided at the bottom of the third transformation stage 506.

FIG. 6 provides a schematic illustration of a current to voltage conversion in approach #3, in accordance with some embodiments of the present disclosure. In particular, FIG. 6 illustrates operation of the pseudo-resistor shown in FIG. 5 where the sensor current $I_{IN}$ is forced to go through the gate oxide of a MOS transistor (indicated in FIG. 6 as Msense) because the gate of the transistor Msense is grounded (as shown in FIG. 6). For an appropriate range of voltages and currents (where the currents are typically very small currents), the tunneling current through the gate oxide of the transistor Msense can be related to the voltage potential across the gate oxide, by the equation shown at the bottom of FIG. 6 (repeated from the bottom of the first transformation stage 502 shown in FIG. 5), enabling use of the transistor Msense to sense the leakage current. Such a voltage Vsense is expected to be linear at a certain range. Though the transistor Msense is constructed as a MOS transistor, the transistor Msense is applied as a two-terminal device, one side being the gate electrode and the other side being the source, drain, and well, together. Such a transistor can be modeled as a relatively large resistance between these two terminals, as needed for the first transformation stage 502 shown in FIG. 5.

FIG. 6 further illustrates Cbypass, which is a bypass capacitor which may, optionally, be used to decouple clock ripple.

Figure 7:
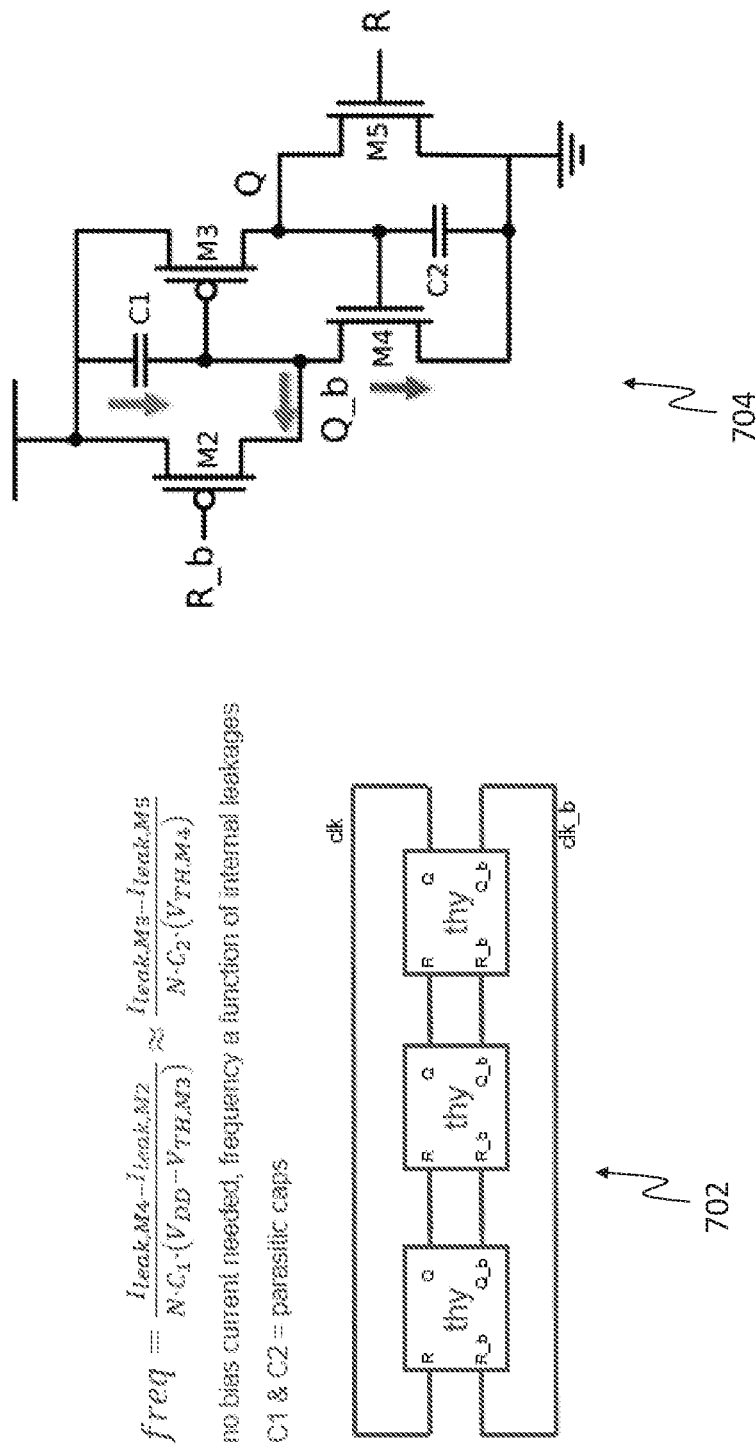
FIG. 7 provides a schematic illustration of a relaxation oscillator.

FIG. 7 provides a schematic illustration of a relaxation oscillator which could be used in approach #3. A circuit 702 shown in FIG. 7 illustrates a relaxation oscillator design, which may be an example of an ultra-low-power (ULP) oscillator, used to measure the voltage drop Va-Vb on the gate oxide of the transistor Msense. As shown in FIG. 7, in some embodiments, the relaxation oscillator 702 may include three interconnected sub-blocks. One sub-block is shown with a circuit 704 on the right side FIG. 7, where either one or both of the capacitors C1 and C2 are charged through currents at the Q and Q_b nodes. As these capacitors charge, the voltages at Q and Q_b change, eventually reaching the threshold of either one or both of MOS transistors M3 and M4. As M3 and/or M4 begin to turn on, positive feedback drives the other node to charge faster as well. Node Q approaches the supply voltage, and Q_b approaches ground. The Q and Q_b nodes are connected to the reset R, and R_b nodes of the other sub-blocks of the circuit 702, so that each block triggers the action of the next. Together, the three sub-blocks of the circuit 702, which, in various embodiments, could be any other "odd" number of blocks, will result in an ongoing oscillation. It should be noted that, in the example of FIG. 7, there is no signal input and the oscillation frequency is determined by the leakage currents of the transistors.

Figure 8:
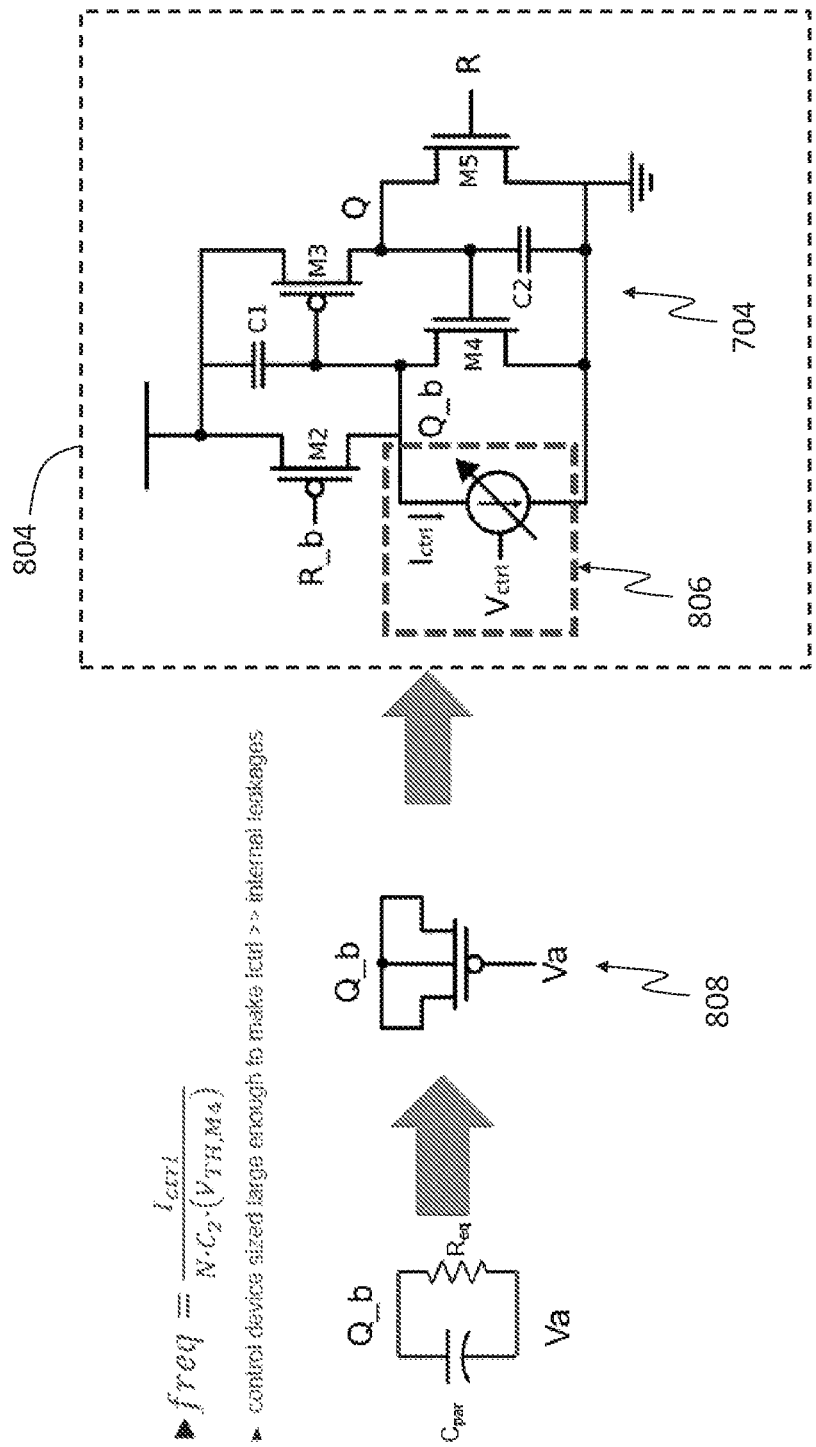
FIG. 8 provides a schematic illustration of using a relaxation oscillator for current to voltage conversion in the third proposed approach, in accordance with some embodiments of the present disclosure.

FIG. 8 provides a schematic illustration of using a relaxation oscillator for current to voltage conversion in the third proposed approach, in accordance with some embodiments of the present disclosure. FIG. 8 provides an improved (fine-tuned) version of the relaxation oscillator as shown in FIG. 7, where the right side of FIG. 8 illustrates a circuit 804 which may be used as one sub-block 704 of the oscillation circuit 702 as shown in FIG. 7. In particular, the circuit 804 is shown in FIG. 8 to include the sub-block 704 shown in FIG. 7, and further include an additional circuit 806 configured to generate voltage-controlled current which is then provided as a charging current for the capacitor C1 of the oscillator circuit 704 of the circuit 804.

FIG. 8 further illustrates that the circuit 806 comprises an additional pseudo-resistor, indicated in FIG. 8 as a MOS transistor 808, which pseudo-resistor is connected so as to contribute current to the charging of capacitor C1. The oscillator frequency of the oscillation circuit 804 will be affected by this additional current, and since this current is determined by the voltage applied to the pseudo-resistor 808, the frequency of the oscillator will be related to the voltage on the other side of the pseudo-resistor (shown as Va, as an example, in FIG. 8).

Figure 9:
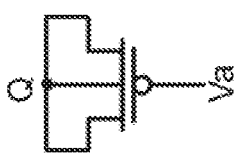
FIG. 9 provides a schematic illustration of a voltage-to-current conversion in the third proposed approach, in accordance with some embodiments of the present disclosure.

FIG. 9 provides a schematic illustration of a voltage-to-current conversion in approach #3, in accordance with some embodiments of the present disclosure. In particular, FIG. 9 illustrates equations describing how the use of pseudo-resistors in two places in the overall circuit, as described above, can cancel some of the possible non-linearities and other issues with using the pseudo-resistors. Because in the first use, shown in FIG. 6, a pseudo-resistor converts a current into a voltage, and, in the second use, shown in FIG. 8, another pseudo-resistor does the opposite and converts a voltage into a current, imperfections in the transfer function will tend to cancel, to the degree that the two pseudo-resistors substantially match in their characteristics. This leads to a relatively linear overall transfer function from the original sensor signal current $I_{IN}$ into the final oscillator output frequency. Because the oxide tunneling current characteristics of the pseudo-resistors are very sensitive to the geometries of the structure, this "cancellation" of non-linearities, from devices which may be fabricated on a given wafer in close proximity, is valuable.

Proposed Approach #4: Converter Exploiting Direct Sensor Current Drive and Relaxation Oscillator While approach #3 is particularly suitable for relatively small currents, in the pA range, approach #4 may be targeted at somewhat larger sensor signal currents, e.g., up to the nanoAmpere (nA) range. Instead of the double transformation used in approach #3 (i.e., transformation of current to voltage, then back to current), this approach is based on applying the sensor signal current directly (i.e., without using the pseudo-resistors) to the current-controlled-oscillator circuit. This may avoid any of the non-linearities and other constraints coming from the use of the pseudo-resistors. Since the current is used directly, only one oscillator may be used and then no frequency "differencing" is necessary. An additional possible refinement to approach #4 may include the use of simple inverters to provide the feedback necessary to insure oscillation. This may further reduce the circuit complexity, and area consumed, which are critical metrics for nanogap sensor arrays with millions of sensors.

Figure 10:
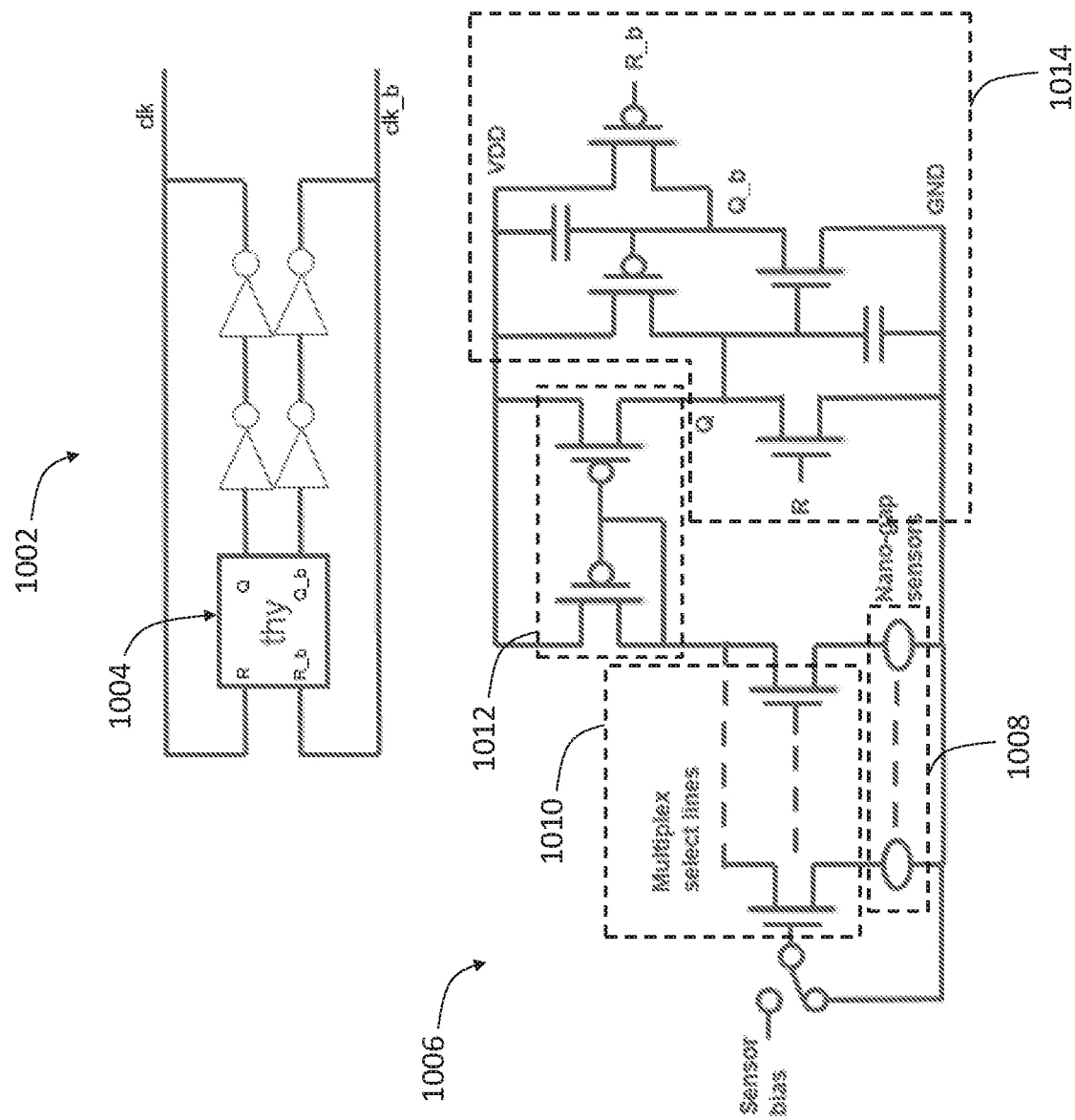
FIG. 10 provides a schematic illustration of a first system for implementing a fourth proposed approach for analog-to-digital conversion of data acquired by nanogap sensors, in accordance with some embodiments of the present disclosure.

One circuit proposal for the approach #4 is shown in FIG. 10. An upper circuit 1002 shown in FIG. 10 illustrates a simplified circuit with only a single capacitor charging sub-circuit 1004, which sub-circuit is shown within a nanogap sensor system 1006 shown in the lower portion of FIG. 10. The actual sub-circuit operation may be substantially analogous to that described with reference to FIG. 7 (which descriptions, therefore, in the interests of brevity, are not repeated), though the sub-circuit shown in FIG. 8 has been re-drawn slightly for cleanliness. The nanogap sensors are shown at the bottom of the nanogap sensor system 1006 as nanogap sensors 1008 (which could, e.g., be a part of the nanogap sensor array 202), where optional input signal multiplexing is also shown. At any point in time, a particular nanogap sensor (indicated by the small ovals at the bottom of the nanogap sensor system 1006) may be selected by the "multiplexing" transistor out of a plurality of multiplexing transistors of a multiplexing transistor arrangement 1010 shown in FIG. 10. Current from the selected sensor may pass through the multiplexing transistor, while other multiplexing transistors may be turned off, reducing or altogether preventing confounding currents from the other sensors from reaching the relaxation oscillator (shown in FIG. 10 as a relaxation oscillator circuit 1014, analogous to the circuit 704, described above). Thus, each of the nanogap sensors in the nanogap sensor system 1006 may have an associated multiplexing transistor, thus realizing multiplex select lines for converting the current generated by a particular nanogap sensor. The selected multiplexing transistor may be activated by setting its gate voltage to a pre-determined "bias" value, which forces a relatively fixed voltage across the sensor, such that the resulting sensor current may accurately reflect the conductivity of the sensor.

In other embodiments, the multiplexer arrangement 1010 as shown in FIG. 10 may further include so-called "unselect" or "dump" transistors to sink currents from deselected sensors, if needed. This is not specifically shown in FIG. 10, but the multiplexer arrangement similar to that described with reference to FIGS. 11 and 12 may be used as the multiplexer arrangement 1010 of FIG. 10.

In the embodiment of approach #4 shown in FIG. 10, the "cascode" topology of the multiplexing transistor may convey the sensor current to a "current mirror" structure 1012, composed of the two transistors as shown in FIG. 10. Because these two P-type (PMOS) devices have their gates and sources each connected together, as shown in the structure 1012, they will conduct equal currents. The PMOS device shown in FIG. 10 on the left side of the structure 1012 receives the sensor current, so the PMOS device shown in FIG. 10 on the right side of the structure 1012 can deliver a copy of the sensor current to the node Q of the oscillator, resulting in a corresponding oscillation frequency. By use of the current mirror 1012, the voltage waveforms on the node Q may be isolated from the sensor, and the sensor may substantially only sense the stable biasing voltage.

Figure 11:
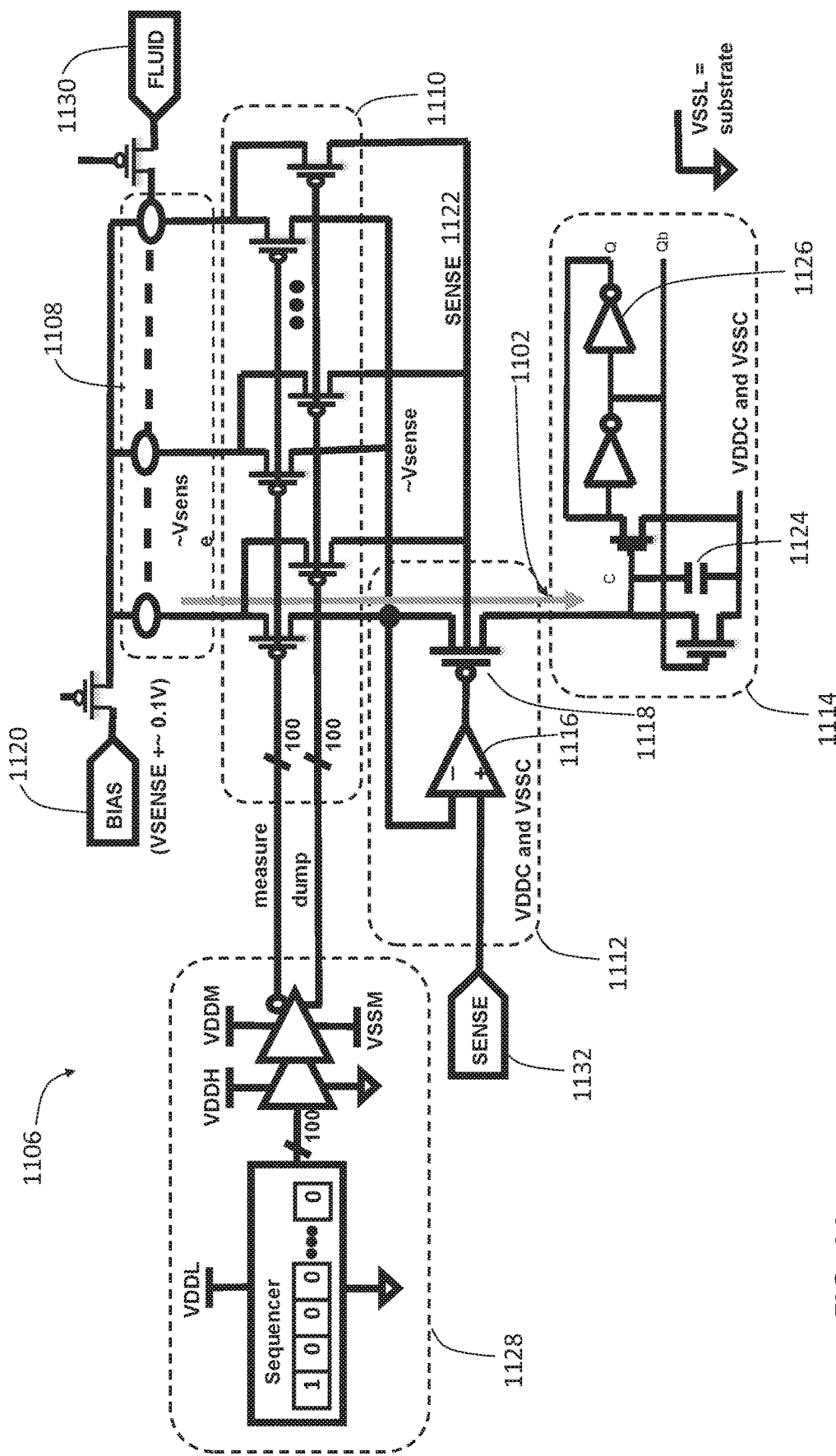
FIG. 11 provides a schematic illustration of a second system for implementing a fourth proposed approach for analog-to-digital conversion of data acquired by nanogap sensors, in accordance with some embodiments of the present disclosure.

FIG. 11 provides a circuit proposal for the approach #4 which may be used as an alternative to that shown in FIG. 10. Similar to FIG. 10, FIG. 11 illustrates a nanogap sensor system 1106 that may include one or more, typically a plurality of nanogap sensors 1108 (which could, e.g., be a part of the nanogap sensor array 202), an optional input signal multiplexing using a multiplexing transistor arrangement 1110, and a relaxation oscillator circuit 1114. A readout input node (or, simply, readout input) 1102 may be defined as a node for receiving an input signal for the relaxation oscillator 1114, the input signal indicative of the current generated by one of the one or more nanogap sensors 1108 being readout. Similar to the relaxation oscillator 1014 of FIG. 10, the relaxation oscillator 1114, coupled to the readout input 1102, may be configured to oscillate with an oscillation frequency indicative of the input signal.

Unlike the nanogap sensor system 1006 shown in FIG. 10, FIG. 11 illustrates that, in some embodiments, the system for nanogap sensor readout may include an active cascode 1112. Such an active cascode 1112 may include an amplifier 1116 and a cascode transistor 1118, and may couple the one or more nanogap sensors 1108 and the relaxation oscillator 1114 (i.e., the active cascode 1112 shown in FIG. 10 may be used instead of the current mirror 1012 shown in FIG. 10). For example, the active cascode 1112 may be provided between the nanogap sensors 1108 and the readout input 1102, as shown in FIG. 11. For the embodiments where the multiplexer 1110 is used, the active cascode 1112 may be coupled between the multiplexer 1110 and the readout input 1102.

When used, the active cascode 1112 may advantageously enable a "flow-through" signal path (e.g., from one of the nanogap sensors 1108, optionally to the multiplexer 1110, then to the active cascode 1112, and finally to the relaxation oscillator 1114) for current signals generated by the nanogap sensors 1108 to avoid offset/gain errors which may sometimes be associated with a current mirror over a wide dynamic range. As described in greater detail below, using the active cascode 1112 may be particularly advantageous at the low signal currents, where transistors may be operating in weak inversion and accuracy of current mirrors in replicating nanogap sensor signal currents may be sub-optimal.

In some implementations, it may be desirable to force a controlled voltage across sensor electrodes of the nanogap sensors. To that end, a bias electrode of a given one of the nanogap sensors may be driven from a voltage source (e.g. a voltage source shown in FIG. 11 as a bias 1120; an analogous bias source may also be used in the embodiment shown in FIG. 10, although not specifically shown there), and it may be desirable to maintain a "virtual ground" on a sense electrode of a given one of the nanogap sensors. Some solutions to achieving controlled voltage across sensor electrodes may include using a "cascode" device where the gate voltage is pinned and source varies little with current. However, when such circuits operate at low currents, transistors may be in "weak inversion." Gate-to-source potential may vary by about 80 mV/decade, and 80 dB dynamic range may corresponds to a 320 mV change.

The active cascode 1112 may be configured to serve as a current conveyor to help control the nanogap sensor excitation and advantageously isolate the nanogap sensors from the relaxation oscillator waveforms. The amplifier 1116 gain, through its feedback loop, may be configured to monitor the desired sense voltage 1132, and apply an appropriate signal to the cascode transistor 1118 to compensate for the cascode transistor gate-to-source potential variation due to changes in the sensor current. In other words, the active cascode 1112 may help maintaining a carefully controlled voltage across the nanogap sensors 1108 despite varying sensor conductance (where varying sensor conductance may result in varying sensor current). The voltage across the sensors becomes the difference between the bias voltage 1120, and the sense voltage 1132.

In some implementations of conventional cascode circuits, a cascode transistor may introduce a pole in the loop transmission, whose frequency may vary with the transconductance (gm) of the transistor. The gm may vary with the signal current, and thus the pole frequency may also vary, over several orders of magnitude. At higher currents, this pole may be at too high a frequency to stabilize the cascode amplifier, so an additional pole may be needed. But then at some lower currents, both poles together may lead to poor stability.

To address at least some of these issues, the cascode 1112 may be designed by adding a pole that is dependent on signal current and that only becomes active at higher signal currents. Such a design may be elegantly implemented within amplifier 1116 by using another transistor, e.g., a MOS transistor, with carefully selected gate capacitance, so that the gate capacitance becomes significant only when the gate-source voltage is above a certain threshold. With such implementation, the gate voltage of the cascode transistor 1118 may naturally vary with the signal current from the nanogap sensors 1108, as provided over the sense line 1132 (e.g., about 80 mV per decade, in weak inversion), and can be used to "drive" the gate of the compensation transistor.

To that end, in some embodiments, the amplifier 1116 of the active cascode 1112 may be configured to use adaptive compensation for stability over the full dynamic range of nanogap sensor currents, e.g., currents from pA to more than tens of nA.

In some embodiments, the relaxation oscillator circuit 1114 may be analogous to the circuit 704, described above. In general, the relaxation oscillator 1114 (or the relaxation oscillator 1014 shown in FIG. 10) may be configured to oscillate with an oscillation frequency indicative of the input signal to the oscillator, the input signal indicative of the current generated by the nanogap sensor being readout. Since the input signal is indicative of the current generated by the one of the one or more nanogap sensors 1108/1008, the oscillation frequency of the relaxation oscillator 1114/1014 is also indicative of the current generated by the one of the one or more nanogap sensors.

In some embodiments, the relaxation oscillator 1114/1014 may be a relatively simple current-controlled relaxation oscillator per channel, which, when coupled with a counter (e.g., the counter 1306 shown in FIG. 13, although such a counter is not specifically shown in FIGS. 10 and 11) may convert the analog input current into a digital value. In such an oscillator, the input current signal may be transformed, by the relaxation oscillator, into increasing phase of the oscillator, quantized to output "cycles." The cycles are counted by the counter to accumulate the digitized input signal over a given measurement interval. Such an approach to converting the current generated by a nanogap sensor from analog to digital domain advantageously reduces or eliminates the need for large sampling capacitors and/or attenuation of said current, which needed to be used in prior art approaches described above. Using a relaxation oscillator as described herein advantageously enables use of only a relatively small capacitor in the oscillator itself (i.e., no integration of the analog input is performed on the capacitor(s), instead the integration of the input may be performed through digital accumulation in the counter).

In particular, the phase of the oscillator 1114/1014 may represent the integral of the input current, i.e., the charge indicative of the input current from a nanogap sensor being readout. In the digital output from the relaxation oscillator 1114/1014 this phase becomes quantized to integer cycles. Then, by accumulating the total number of cycles in the counter (e.g., the counter 1306 shown in FIG. 13), the input signal is integrated throughout the measurement interval. Thus, using a relaxation oscillator in the readout scheme described herein allows, first, digitizing the input current, and then integrating the result in digital form, i.e., this approach may be referred to as a "first digitize then integrate" approach. This is fundamentally different from conventional readout schemes used for nanogap sensors in which the input current from the sensors is first integrated in analog form using capacitors, and is digitized after the integration, i.e., an approach which may be referred to a "first integrate then digitize" approach that involves, first, integrating all the signal for a given measurement, and then only afterwards digitizing with a high-dynamic-range ADC and requires using prohibitively large capacitors. Instead, the approach described herein, namely, the approach of digitizing the signal with a higher bandwidth, then integrating (accumulating) the digitized results advantageously enables using only a very small capacitor 1124 in the oscillator 1114, because "integration" of the input is performed through digital accumulation in counter. The higher sample rate in the digitizer (or even an effectively continuous process) may advantageously reduce the duration of each digitization, reducing the charge per quantization and therefore the size of any capacitors used within the relaxation oscillator 1114. Accumulation of the digitized results involves a digital counter which size grows only logarithmically with the length of the overall measurement time. In some embodiments, the digital decimation (averaging) using a relaxation oscillator and a digital counter may effectively improve the signal-to-noise of the digitizer, so a lower resolution (noisier) quantizer may be sufficient, compared to conventional conversion approaches used with nanogap sensors.

As shown in FIG. 11, the relaxation oscillator 1114 may further include one or more logic delay elements 1126 (two of which are shown in the example of FIG. 11), which may be used to reset the capacitor 1124. An implementation of the relaxation oscillator circuit 1114 as shown in FIG. 11 has a potential for requiring very small area on a chip as the oscillator 1114 may use only one "relaxation" stage, plus small logic delay elements 1126 for capacitor reset. Such an implementation is expected to scale well into finer lithographic nodes as fabrication technology continues developing and aligns well with expected nA-level sensor currents from the nanogap sensors 1108.

Turning to the details of the multiplexer arrangement 1110, similar to FIG. 10, for the embodiment shown in FIG. 11, at any point in time, a particular nanogap sensor 1108 (indicated by the small ovals at the top of the nanogap sensor system 1106) may be selected by the "multiplexing" transistor out of a plurality of multiplexing transistors of the multiplexing transistor arrangement 1110. In some embodiments, such transistors may be implemented as metal-oxide-semiconductor field-effect transistors (MOSFETs). Current from the selected sensor 1108 may pass through the corresponding multiplexing transistor, while other multiplexing transistors (i.e., multiplexing transistors corresponding to other sensors) may be turned off, reducing or altogether preventing confounding currents from the other sensors from reaching the relaxation oscillator 1114. Thus, each of the nanogap sensors in the nanogap sensor system 1106 may have an associated multiplexing transistor, thus realizing multiplex select lines for converting the current generated by a particular nanogap sensor. In some embodiments, the selected multiplexing transistor may be activated by setting its gate voltage to a pre-determined "bias" value, which forces a relatively fixed voltage across the sensor, such that the resulting sensor current may accurately reflect the conductivity of the sensor.

The plurality of transistors of the multiplexer 1110 may be referred to as a "transistor switch network" or "switching transistors." Having the switching transistors coupled to the nanogap sensors enables each sensor output/sense electrode (i.e., the electrode on which the signal is sensed) to be independently connected to the signal chain by means of a respective transistor, which may, therefore, also be referred to as an "access transistor." In various embodiments, for each nanogap sensor 1108, a sense electrode of the nanogap sensor 1108 may be coupled to a source/drain (S/D) terminal of the corresponding one of the plurality of access transistors. As known in the art, source and drain terminals of a MOSFET may be interchangeable. Therefore, as used herein, the notation of "a S/D terminal" may be used to indicate that said terminal may be either a source terminal or a drain terminal.

In some implementations, leakage current of transistors used in the multiplexer 1110, where the term "leakage current" refers to the current flowing between the source and drain at the "off" state of the transistor, may be problematic in readout of a selected nanogap sensor. In particular, leakage currents of various transistors of the multiplexer 1110 associated with unselected nanogap sensors may contribute to the current reaching the readout input node 1102. To overcome this issue, in some embodiments, instead of only using one transistor per nanogap sensor 1108, the multiplexer 1110 may include a pair of transistors. Thus, the multiplexer 1110 may include a first plurality of transistors and a second plurality of transistors, where each one of the nanogap sensors 1108 is associated with, by being coupled to, one transistor of the first plurality and one transistor of the second plurality. During operation of such a multiplexer, for each individual nanogap sensor 1108 of the nanogap sensor array, when the corresponding one of the first plurality of transistors is on, the corresponding one of the second plurality of transistors is off, and vice versa. The transistors of the first plurality may be referred to as "pass transistors" and the transistors of the second plurality may be referred to as "dump transistors" to indicate that only transistors of one of these two sets of transistors are used to pass the current that is then to be readout/sensed by the relaxation oscillator. Thus, each nanogap sensor is coupled to one pass transistor and one dump transistor, with one-to-one correspondence between nanogap sensors and pass transistors, and with one-to-one correspondence between nanogap sensors and dump transistors. The multiplexer 1110 of FIG. 11 already provides an illustration of two transistors per nanogap sensor 1108, with FIG. 12 providing further details of the multiplexer arrangement 1110.

Such pass and dump may be included in the multiplexer to reduce or eliminate subthreshold leakage currents. Namely, when a given nanogap sensor is not being read, i.e., when the pass transistor corresponding to that nanogap sensor is not selected and is off, its' corresponding dump transistor is activated (i.e., is on), to shunt the sensor current away, maintaining a negligible voltage across the unselected pass transistor, and thus negligible subthreshold leakage current through the pass transistor, that would otherwise confound the measurement of another sensor.

Figure 12:
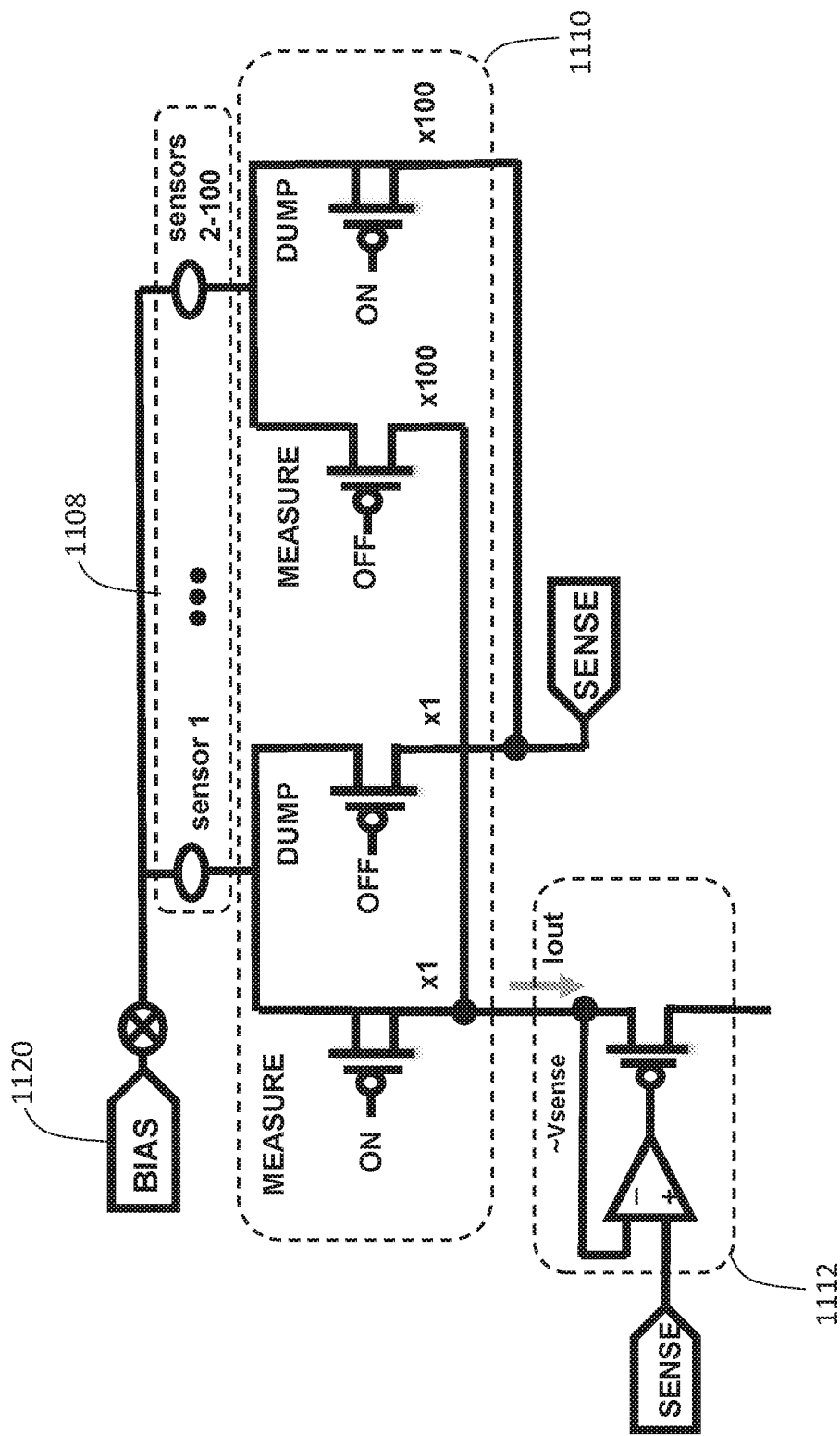
FIG. 12 provides a schematic illustration of dump transistors used in a multiplexing scheme for readout of data from a plurality of nanogap sensors, in accordance with some embodiments of the present disclosure.

In some embodiments, each of the pass and dump transistors may be MOSFETs, as shown in FIGS. 11 and 12. In some embodiments, during operation, for each individual nanogap sensor 1108, a sense electrode of that nanogap sensor may be coupled to a first S/D terminal of the corresponding dump transistor, and a second S/D terminal of the corresponding dump transistor may be held at a potential that is substantially equal, e.g., deviates by less than about 20%, or by less than about 10%, or by less than about 5%, to a voltage on the sense electrode (Vsense). Furthermore, the well terminals of all pass and dump transistors may be held at a potential 1122 that is substantially equal to a voltage on the sense electrode. In this manner, the multiplexer transistor junctions may be "bootstrapped" to (nearly) the same potential as the sensor voltage Vsense in an attempt to avoid junction leakage currents because with substantially zero voltage across the source-well and drain-well regions, there will be no leakage in the pass transistors. As is well known, transistor junctions are between the source and the well, and the drain and the well of a transistor. Keeping the source and drain potentials substantially the same allows reducing or altogether eliminating subthreshold leakage, while bootstrapping the well potential also to that value reduces or eliminates the junction leakages.

In some embodiments, the transistors of the multiplexer 1110 may be driven with a multiplexer driver 1128, shown in FIG. 11. Such a driver may be configured to supply suitable gate potentials to the plurality of pass transistors and the plurality of dump transistors in the multiplexer 1110, thereby controlling which sensor is being measured. The multiplexer may include a counter or shift-register, so that a small number of digital control signals enable the ensemble of sensors to be measured in sequence. The voltages applied to the gates of the pass and dump transistors may be chosen to minimize the gate oxide fields, thereby minimizing leakage errors from oxide tunneling currents, while still insuring acceptably low "on" resistances, and sufficiently high "off" resistances, in the multiplexer transistors.

In some embodiments, the nanogap sensor system 1106 may further include one or more fluidic channels for providing one or more fluid analytes to the one or more nanogap sensors 1108, and applying a desired voltage potential 1130 to the fluid.

To summarize, approach #4 uses a relaxation oscillator similar to approach #3, but using just one oscillator per channel, and the sensor current is applied "directly" to charge internal capacitors. Conversion result is encoded in the frequency of the relaxation oscillator, with the output frequency being proportional to sensor current. Such implementation may avoid pseudo-resistor non-linearity and mismatch, has potential for very small area, and is expected to scale well into finer lithographic nodes. In addition, the oscillator may be implemented with only one relaxation stage, while others could be simple inverters. Any of the relaxation oscillators shown in FIG. 10 or 11, or any other architecture of relaxation oscillators as known in the art, may be used as a current-controlled relaxation oscillator, coupled to a counter, for converting the analog input current into a digital value according to the approach #4. Unless specified otherwise, description of embodiments of FIG. 11 are applicable to FIG. 10 even though they may not be specifically provided for FIG. 10, e.g., descriptions of the FLUID 1130 or the pass-dump transistor arrangement of the multiplexer 1110.

Various methods of operating a system that includes one or more, typically an array of, nanogap sensors for evaluating one or more fluid analytes, and utilized relaxation oscillators for analog-to-digital conversion of sensor currents, e.g., any of the systems described above, are also within a scope of the present disclosure.

An example method of operating such a system may include applying one or more signals to one or more selector transistors corresponding to a particular nanogap sensor of the array to select that nanogap sensor for readout. Application of such signals may include application of signals to turn pass and dump transistors of different nanogap sensors of the array in the manner described above. The method may further include determining an oscillation frequency of the relaxation oscillator coupled to the selected nanogap sensor (where said "coupling" may involve coupling via a multiplexer and an active cascode as described above). The method may also include estimating/evaluating the current generated by the selected nanogap sensor based on the determined oscillation frequency (since the relaxation oscillator is configured to oscillate with the oscillation frequency indicative of the current generated by the selected nanogap sensor). The method may further include determining presence and/or amount of at least one of the one or more fluid analytes based on the determined current.

Example Systems for Implementing Proposed Approaches

Figure 13:
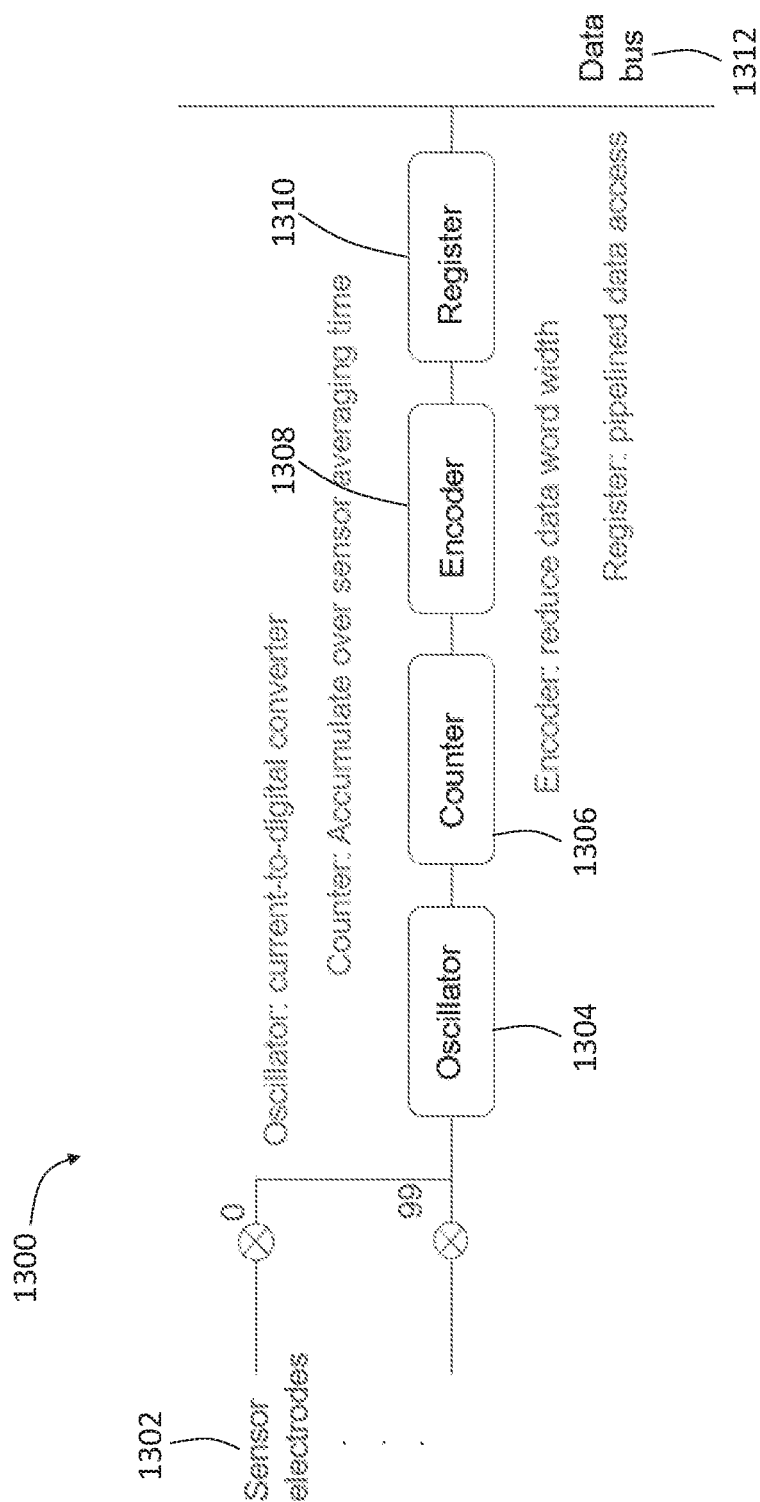
FIG. 13 provides a schematic illustration of a channel architecture for implementing various proposed approaches for analog-to-digital conversion of data acquired by nanogap sensors, in accordance with some embodiments of the present disclosure.

FIG. 13 provides a schematic illustration of an overall channel architecture 1300 for implementing various proposed approaches for analog-to-digital conversion of data acquired by nanogap sensors, in accordance with some embodiments of the present disclosure.

As shown in FIG. 13, the system 1300 includes an array of nanogap sensors 1302, implementing one channel of the array 202 shown in FIG. 2. Considerations provided above with reference to the nanogap sensors 302 shown in FIG. 3 are applicable to the nanogap sensors 1302 and, therefore, not repeated.

As also shown in FIG. 13, the system 1300 further includes an oscillator 1304 which functions as an ADC converting the analog current signal from the sensors 1302 to a digital signal, according to any embodiments of the four approaches described above.

The system 1300 further includes a counter 1306, which may be used to implement any of the counters illustrated in the ADC systems according to any embodiments of the four approaches described above.

The system 1300 may further, optionally, include an encoder 1308 which may be used to reduce data word width of the digital signal generated from the nanogap sensor current. Depending on the details of the biological or chemical analysis being performed using the nanogap sensors, it may not be necessary to communicate the full resolution of the digitized sensor signals. For example, a logarithmic, another non-linear representation, or any other representation of the sensor signal indicative of the information sought from the sensor measurements may be equally informative. By encoding the counter output in such a fashion, the number of bits in the representation may, advantageously, be reduced. Reducing the number of bits necessary simplifies the subsequent logic complexity, and lowers the data rate necessary to transmit the results off the chip. In some embodiments, the encoder 1308 may be configured to reduce a data word width of the digital representation of the converted input current signal based on one or more parameters of one or more nanogap sensors 1108. For example, in some applications, the final information sought from the sensor measurements may be as simple as the particular DNA base pair, i.e., just one of four possibilities, which is what the encoder 1308 may be configured to represent, e.g. by encoding one of the two-digit values to represent these 4 DNA base pair possibilities—00, 01, 10, or 11. Of course, for other applications much more detailed information might be desired. If the final result is simple to deduce, it may be preferred to make that deduction at this point in the signal chain, so that much less data needs to be transmitted "downstream", reducing the subsequent data widths and data rates.

The system 1300 may also include a register 1310 configured to provide pipelined data access to a data bus 1312. The register can maintain the result of a given sensor measurement while a subsequent sensor is being measured, so that the former result can be communicated off the chip. This may allow overlap between measurements and communication, so that each can proceed without blocking the other, maximizing the overall throughput of the system. In some embodiments, the encoder 1308 may be coupled between the counter 1306 and the register 1310. In the embodiments where the encoder 1308 is not implemented, the register 1310 may be coupled to the counter 1306.

The architecture shown in FIG. 13 is a highly digital signal chain, which, advantageously, makes it easy to scale to dense process nodes.

Figure 14:
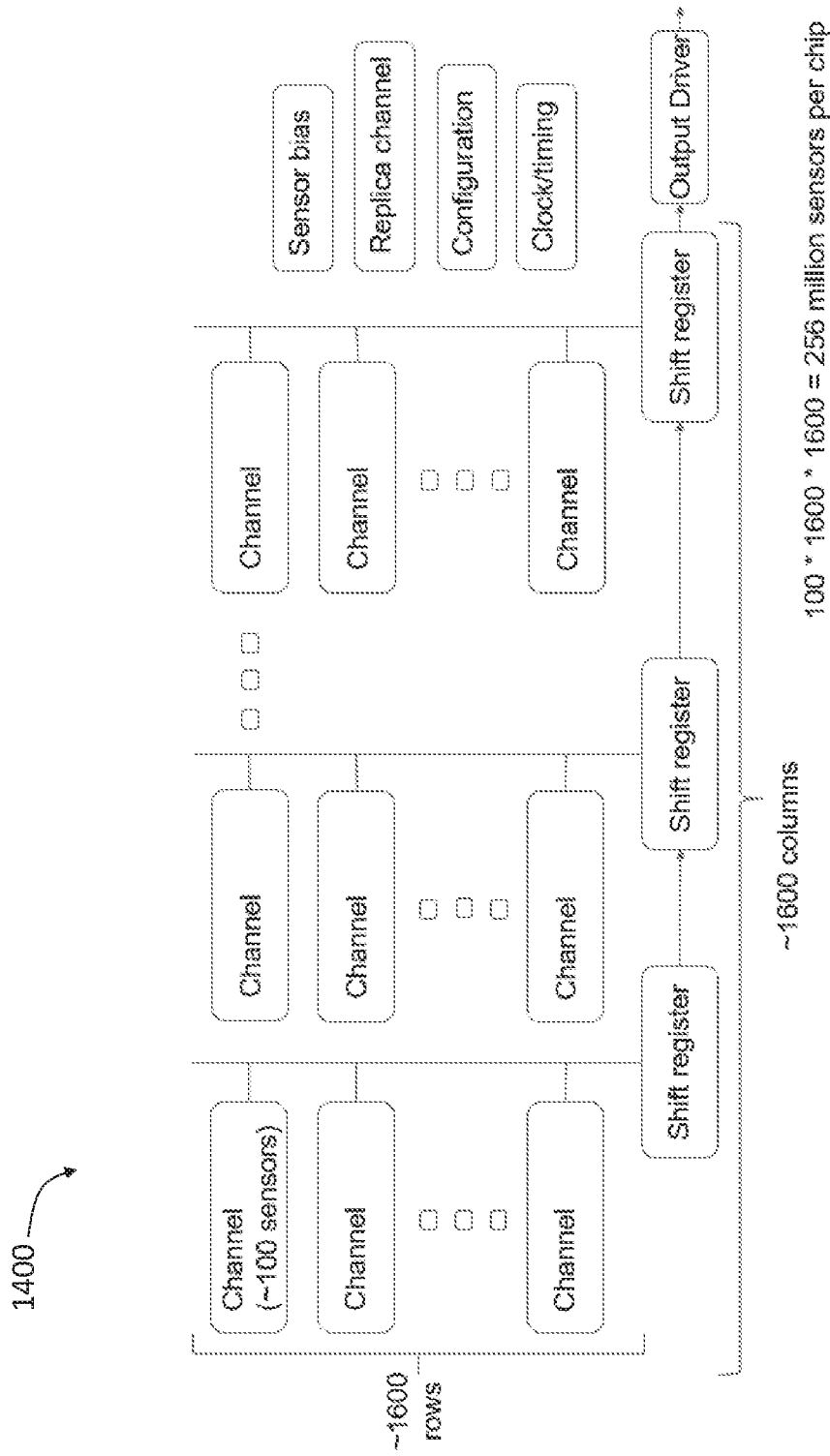
FIG. 14 provides a schematic illustration of an overall readout architecture for implementing various proposed approaches for analog-to-digital conversion of data acquired by nanogap sensors, in accordance with some embodiments of the present disclosure.

FIG. 14 provides a schematic illustration of an overall readout architecture 1400 for implementing various proposed approaches for analog-to-digital conversion of data acquired by nanogap sensors, in accordance with some embodiments of the present disclosure. Because it may be desired to integrate enormous numbers of sensors on a single chip for efficient and accurate analytical results, many of the channels described in FIG. 13 can be aggregated into a larger array. FIG. 14 shows how a collection of such channels may be interconnected in some embodiments of the present disclosure to efficiently communicate the digital results of the many sensors off the chip.

Also included in FIG. 14 are additional functional blocks to improve performance at the system level. First, the sensor bias voltage control has been discussed earlier with reference to FIGS. 10 and 11. Second, one or more "replica" channels can be included to calibrate the current-to-digital scale factor of the oscillators. While the fabrication capabilities of monolithic manufacturing technologies deliver good matching between nominally identical devices on a chip, the absolute "gain" can vary significantly, and is also sensitive to temperature. By including "replica" or "reference" channels, where a known signal current can be applied from an external source, it becomes possible to measure the resulting "reference" response, and (digitally) compensate for the (very similar) response in the signal channels.

Finally, it is further possible to add additional data bits to the overall "data packet", to aid in clock synchronization, and provide error detection against data corruption. All these additional "system level" features would possibly be controlled through one or more configuration registers, to make the chip flexible across a variety of applications.

Figure 15:
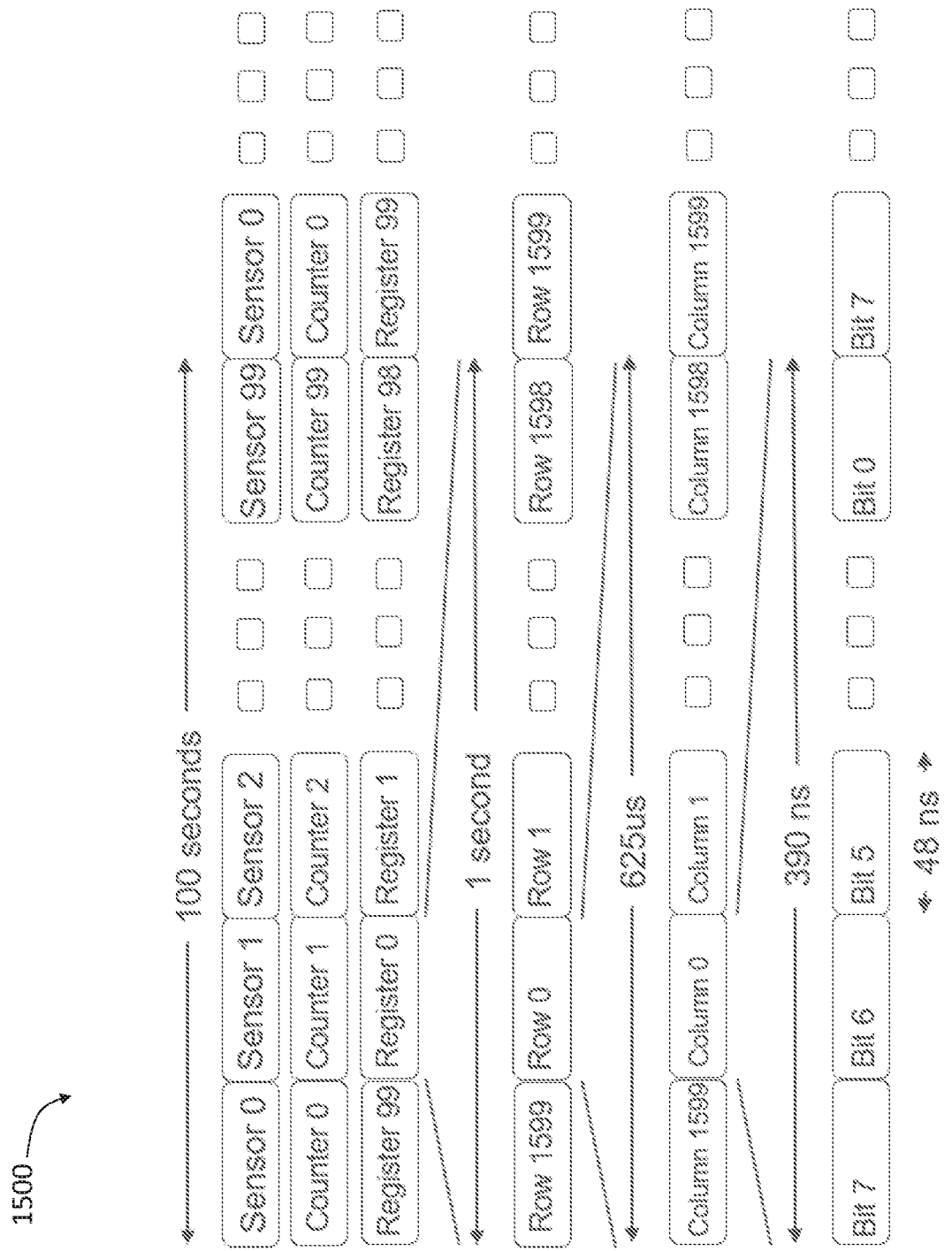
FIG. 15 provides a schematic illustration of a timing architecture for implementing various proposed approaches for analog-to-digital conversion of data acquired by nanogap sensors, in accordance with some embodiments of the present disclosure.

FIG. 15 provides a schematic illustration 1500 of a timing architecture for implementing various proposed approaches for analog-to-digital conversion of data acquired by nanogap sensors, in accordance with some embodiments of the present disclosure. FIG. 15 illustrates that multiple levels of multiplexing are possible with the nanogap sensor arrays as described herein: bits of a word, words by columns, columns by rows, rows by sensors, sensors in a channel. Pipeline registers may be used at each stage of multiplexing, to avoid setup/hold time challenges.

Figure 16:
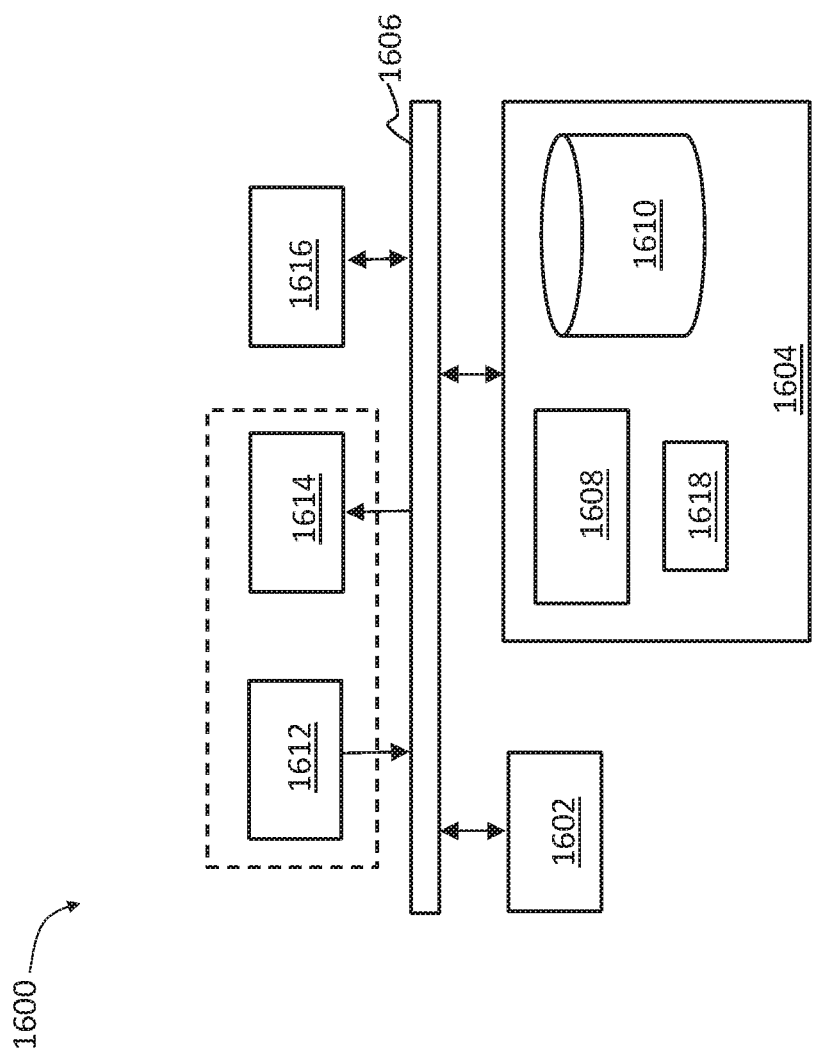
FIG. 16 provides a block diagram illustrating an example data processing system for carrying out analog-to-digital conversion and/or molecular evaluation of sample analytes using any of the nanogap sensor systems disclosed herein, according to some embodiments of the present disclosure.

FIG. 16 provides a block diagram illustrating an example data processing system for carrying out analog-to-digital conversion and/or molecular evaluation of sample analytes using any of the nanogap sensor systems disclosed herein, according to some embodiments of the present disclosure. Such a data processing system could be configured to e.g., function as the sensor logic 210 and at least parts of the ADC 206 described herein or as any other system configured to implement various improved mechanisms related to molecular evaluation of sample analytes using any of the nanogap sensors and arrangements of such sensors disclosed herein.

As shown in FIG. 16, the data processing system 1600 may include at least one processor 1602 coupled to memory elements 1604 through a system bus 1606. As such, the data processing system may store program code within memory elements 1604. Further, the processor 1602 may execute the program code accessed from the memory elements 1604 via a system bus 1606. In one aspect, the data processing system may be implemented as a computer that is suitable for storing and/or executing program code. It should be appreciated, however, that the data processing system 1600 may be implemented in the form of any system including a processor and a memory that is capable of performing the functions described within the present disclosure.

The memory elements 1604 may include one or more physical memory devices such as, for example, local memory 1608 and one or more bulk storage devices 1610. The local memory may refer to RAM or other non-persistent memory device(s) generally used during actual execution of the program code. A bulk storage device may be implemented as a hard drive or other persistent data storage device. The processing system 1600 may also include one or more cache memories (not shown) that provide temporary storage of at least some program code in order to reduce the number of times program code must be retrieved from the bulk storage device 1610 during execution.

Input/output (I/O) devices depicted as an input device 1612 and an output device 1614, optionally, can be coupled to the data processing system. Examples of input devices may include, but are not limited to, a keyboard, a pointing device such as a mouse, or the like. Examples of output devices may include, but are not limited to, a monitor or a display, speakers, or the like. Input and/or output devices may be coupled to the data processing system either directly or through intervening I/O controllers.

In an embodiment, the input and the output devices may be implemented as a combined input/output device (illustrated in FIG. 16 with a dashed line surrounding the input device 1612 and the output device 1614). An example of such a combined device is a touch sensitive display, also sometimes referred to as a "touch screen display" or simply "touch screen". In such an embodiment, input to the device may be provided by a movement of a physical object, such as e.g., a stylus or a finger of a user, on or near the touch screen display.

A network adapter 1616 may also, optionally, be coupled to the data processing system to enable it to become coupled to other systems, computer systems, remote network devices, and/or remote storage devices through intervening private or public networks. The network adapter may comprise a data receiver for receiving data that is transmitted by said systems, devices and/or networks to the data processing system 1600, and a data transmitter for transmitting data from the data processing system 1600 to said systems, devices and/or networks. Modems, cable modems, and Ethernet cards are examples of different types of network adapter that may be used with the data processing system 1600.

As pictured in FIG. 16, the memory elements 1604 may store an application 1618. In various embodiments, the application 1618 may be stored in the local memory 1608, the one or more bulk storage devices 1610, or apart from the local memory and the bulk storage devices. It should be appreciated that the data processing system 1600 may further execute an operating system (not shown in FIG. 16) that can facilitate execution of the application 1618. The application 1618, being implemented in the form of executable program code, can be executed by the data processing system 1600, e.g., by the processor 1602. Responsive to executing the application, the data processing system 1600 may be configured to perform one or more operations or method steps described herein.

Variations and Implementations

Various devices and systems as described herein, e.g., the systems with relaxation oscillators described with reference to FIGS. 10-12, or the arrangements of FIGS. 2 and 13-16, do not represent an exhaustive set of arrangements that may be used to readout data from the nanogap sensors according to any of the four approaches described herein but merely provide examples of such arrangements. Note that the present figures are intended to show relative arrangements of the components therein, and that devices, systems, and arrangements of these figures may include other components that are not illustrated (e.g., various components related to electrical connectivity or thermal mitigation). Furthermore, in various embodiments, any of the features discussed with reference to any of FIGS. 2-16 herein may be combined with any other features to form modified systems that uses nanogap sensors to analyze presence and/or chemical composition of one or more fluid analytes, all of which being within the scope of the present disclosure. Some such combinations are described above, e.g., that the multiplexer arrangement 1010 as shown in FIG. 10 may further include dump transistors as shown in FIG. 11 or 12. In another example of such a combination, a modified system may be substantially the system as shown in FIG. 11 or the system as shown in FIG. 12 but with a relaxation oscillator as shown in FIG. 10.

In the discussions of the embodiments above, sensors, capacitors, comparators, amplifiers, switches, digital core, transistors, and/or other components can readily be replaced, substituted, or otherwise modified in order to accommodate particular circuitry needs implementing molecular evaluation of sample analytes using any of the nanogap sensors and arrangements of such sensors disclosed herein. Moreover, it should be noted that the use of complementary electronic devices, hardware, software, etc. offer an equally viable option for implementing the teachings of the present disclosure.

In one example embodiment, any number of electrical circuits for implementing any of the nanogap sensor arrangements disclosed herein, described herein, may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of DSPs, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities of any of the nanogap sensor arrangements disclosed herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

In another example embodiment, the electrical circuits of the FIGS. may be implemented as stand-alone modules (e.g., a device with associated components and circuitry configured to perform a specific application or function) or implemented as plug-in modules into application specific hardware of electronic devices. Note that various embodiments related to the nanogap sensor arrangements disclosed herein may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, any of the nanogap sensor arrangements disclosed herein may be implemented in one or more silicon cores in ASICs, FPGAs, and other semiconductor chips.

It is also imperative to note that all of the specifications, dimensions, and relationships related to molecular evaluation of sample analytes using any of the nanogap sensor arrangements outlined herein (e.g., the number and the order of fabrication steps, the number of components, etc.) have only been offered for purposes of example and teaching only. Such information may be varied considerably without departing from the spirit of the present disclosure, or the scope of the appended claims. The specifications apply only to some non-limiting examples and, accordingly, they should be construed as such. In the foregoing description, example embodiments have been described with reference to particular method steps and/or component arrangements. Various modifications and changes may be made to such embodiments without departing from the scope of the appended claims. The description and drawings are, accordingly, to be regarded in an illustrative rather than in a restrictive sense.

Note that the activities discussed above with reference to the FIGS. are applicable to any ICs that involve signal processing associated with molecular evaluation of sample analytes using nanogap sensors, particularly those that can execute specialized software programs, or algorithms, some of which may be associated with converting an analog signal to a digital signal and processing such digital signal. Certain embodiments can relate to multi-DSP signal processing, floating point processing, signal/control processing, fixed-function processing, microcontroller applications, etc. In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems utilizing molecular evaluation of sample analytes using nanogap sensors. Moreover, certain embodiments discussed above can be provisioned in digital signal processing technologies for medical imaging, patient monitoring, medical instrumentation, and home healthcare. This could include pulmonary monitors, accelerometers, heart rate monitors, pacemakers, etc. Other applications can involve automotive technologies for safety systems (e.g., stability control systems, driver assistance systems, braking systems, infotainment and interior applications of any kind). In yet other example scenarios, the teachings of the present disclosure can be applicable in the industrial markets that include process control systems that help drive productivity, energy efficiency, and reliability. In consumer applications, the teachings of the molecular evaluation of sample analytes using any of the nanogap sensor arrangements discussed above can be used for products related to personal biotesting.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGS. may be combined in various possible configurations, all of which are clearly within the broad scope of the present disclosure. In certain cases, it may be easier to describe one or more of the functionalities of a given set of flows by only referencing a limited number of electrical elements. It should be appreciated that the electrical circuits of the FIGS. and its teachings are readily scalable and can accommodate a larger number of components, as well as more complicated/sophisticated arrangements and configurations. Accordingly, the examples provided should not limit the scope or inhibit the broad teachings of the electrical circuits as potentially applied to a myriad of other architectures.

Note that in the present disclosure, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same or other embodiments.

It is also important to note that the functions related to molecular evaluation of sample analytes using any of the nanogap sensor arrangements disclosed herein illustrate only some of the possible functions that may be executed by, or within, systems illustrated in the FIGS. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. Note that all optional features of the apparatus described above may also be implemented with respect to the method or process described herein and specifics in the examples may be used anywhere in one or more embodiments.

Parts of various apparatuses for molecular evaluation of sample analytes using any of the nanogap sensor arrangements disclosed herein can include electronic circuitry to perform the functions described herein. In some cases, one or more parts of the apparatus can be provided by a processor specially configured for carrying out the functions described herein. For instance, the processor may include one or more application specific components, or may include programmable logic gates which are configured to carry out the functions describe herein. The circuitry can operate in analog domain, digital domain, or in a mixed-signal domain. In some instances, the processor may be configured to carrying out the functions described herein by executing one or more instructions stored on a non-transitory computer medium.

Note that all optional features of the apparatus described above may also be implemented with respect to the method or process described herein and specifics in the examples may be used anywhere in one or more embodiments.

Select Examples:

Various examples may provide a nanogap sensor readout circuitry 304 as shown in FIG. 3 and/or a nanogap sensor readout circuitry 404 as shown in FIG. 4. Some examples may provide a nanogap sensor readout method as shown in FIG. 5. Some examples may provide a nanogap sensor readout circuitry for the nanogap sensor readout method of FIG. 5 as shown in one or more of FIGS. 6-8. Some examples may provide a nanogap sensor readout method using a system as shown in FIG. 10 or 11. Some examples may provide a nanogap sensor arrangement as shown in any one of FIGS. 3-14.

More specific examples are described below.

Example 1 provides a system for readout of one or more nanogap sensors, the system including a readout input for receiving an input signal, the input signal indicative of a current generated by one of the one or more nanogap sensors; and a relaxation oscillator, coupled to the readout input, for oscillating with an oscillation frequency indicative of the input signal.

Example 2 provides the system according to example 1, where the relaxation oscillator is a current-controlled relaxation oscillator for converting the input signal received in an analog form to a digital signal.

Example 3 provides the system according to examples 1 or 2, where the relaxation oscillator is configured to transform the input signal into a phase of the relaxation oscillator.

Example 4 provides the system according to example 3, further including a counter configured to determine a number of oscillation cycles of the relaxation oscillator, where the number is a digital representation of the input current signal.

Example 5 provides the system according to example 4, further including a register configured to store a count value of the counter.

Example 6 provides the system according to example 4, further including an encoder, coupled to an output of the counter, and configured to reduce a data word width of the digital representation of the converted input current signal based on one or more parameters of the one or more nanogap sensors.

Example 7 provides the system according to example 6, further including a register, coupled to an output of the encoder, and configured to store a digital value provided at the output of the encoder.

Example 8 provides the system according to any one of the preceding examples, where the one or more nanogap sensors includes a plurality of nanogap sensors (i.e., more than one nanogap sensors), and where the system further includes a multiplexer, coupled to the plurality of nanogap sensors and further coupled to the readout input, and configured to provide the input current signal by selecting one of the plurality of nanogap sensors for readout. In other words, the input signal received at the readout input of the system is an input current signal indicative of a current generated by the one of the plurality of nanogap sensors selected by the multiplexer for readout.

Example 9 provides the system according to example 8, where the multiplexer includes a plurality of transistors (which may also be referred to as a "transistor switch network" or "switching transistors"), and where each individual nanogap sensor of the plurality of nanogap sensors is coupled to a corresponding different one of the plurality of transistors (i.e., there is a one-to-one correspondence between the transistors of the multiplexer and the nanogap sensors).

Example 10 provides the system according to example 9, where the transistors include/are MOSFETs.

Example 11 provides the system according to example 10, where, for each individual nanogap sensor of the plurality of nanogap sensors, a sense electrode of the individual nanogap sensor is coupled to a S/D terminal of the corresponding one of the plurality of transistors.

Example 12 provides the system according to any one of examples 9-11, where the plurality of transistors is a first plurality of transistors, the multiplexer further includes a second plurality of transistors, each individual nanogap sensor of the plurality of nanogap sensors is further coupled to a corresponding different one of the second plurality of transistors (thus, each nanogap sensor is coupled to both a corresponding one of the first plurality of transistors and a corresponding one of the second plurality of transistors), and during operation of the system, for each individual nanogap sensor of the plurality of nanogap sensors, when the corresponding one of the first plurality of transistors is on, the corresponding one of the second plurality of transistors is off, and vice versa.

Example 13 provides the system according to example 12, where the transistors of the second plurality of transistors include/are MOSFETs, for each individual nanogap sensor of the plurality of nanogap sensors, during operation of the system, a sense electrode of the individual nanogap sensor is coupled to a first S/D terminal of the corresponding one of the second plurality of transistors, and a second S/D terminal of the corresponding one of the second plurality of transistors is held at a potential that is substantially equal, e.g., deviates by less than about 20%, or by less than about 10%, or by less than about 5%, to a voltage on the sense electrode (Vsense), and further during operation of the system, well terminals of all transistors in the first and second pluralities of transistors are held at a potential that is substantially equal to a voltage on the sense electrode.

Example 14 provides the system according to any one of the preceding examples, further including an active cascode (which may also be referred to as a "current conveyor"), coupled between the one or more nanogap sensors and the readout input, configured to control voltage across sensor electrodes of the one or more nanogap sensors.

Example 15 provides the system according to any one of the preceding examples, further including the one or more nanogap sensors.

Example 16 provides the system according to example 15, further including one or more fluidic channels for providing one or more fluid analytes to the one or more nanogap sensors.

Example 17 provides the system according to any one of the preceding examples, where the one or more nanogap sensors are DNA sensors, each of the one or more nanogap sensors includes at least a first electrode and a second electrode separated by a nanogap, and at least one of the first and the second electrodes includes a SAM of one or more of thiols (R—S—H), di-thiols (H—S—R—S—H), or alkanethiols (e.g., mercapto-propanol or mercaptohexanol), facing the other electrode.

Example 18 provides a method of operating a system that includes an array of nanogap sensors configured to evaluate one or more fluid analytes, the method including applying one or more signals to one or more selector transistors corresponding to a first nanogap sensor of the array to select the first nanogap sensor for readout, and determining an oscillation frequency of a relaxation oscillator coupled to the first nanogap sensor, where the relaxation oscillator is configured to oscillate with the oscillation frequency indicative of a current generated by the first nanogap sensor.

Example 19 provides the method according to example 18, further including determining the current generated by the first nanogap sensor based on the determined oscillation frequency, and determining presence and/or amount of at least one of the one or more fluid analytes based on the determined current.

In further examples, the method according to examples 18 or 19 includes steps for operating the system according to any one of the preceding examples, e.g., for operating the system as described with reference to FIGS. 1-16, in particular, for operating the system as described with reference to FIGS. 10-13.

Example 20 provides a multiplexer for selecting individual nanogap sensors from an array of nanogap sensors configured to evaluate one or more fluid analytes, the multiplexer including pairs of transistors corresponding to individual nanogap sensors in a one-to-one correspondence (i.e., each pair of transistors corresponds to one of the nanogap sensors, and each one of the nanogap sensors corresponds to one of the pairs of transistors), where each pair of transistors includes a pass transistor and a dump transistor, and where, when an individual nanogap sensor is selected for readout, a pass transistor of a pair of transistors corresponding to the individual nanogap sensor is on, a dump transistor of the pair of transistors corresponding to the individual nanogap sensor is off, pass transistors of all other nanogap sensors of the array are off, and dump transistors of all other nanogap sensors of the array are on.

In further examples, the multiplexer according to example 20 may be the multiplexer of, or be included in, the system according to any one of the preceding examples, e.g., the system as described with reference to FIGS. 1-16, and, in particular, the system as described with reference to FIGS. 10-13.

The invention claimed is:

1. A system for readout of one or more nanogap sensors, the system comprising:
   a readout input for receiving an input signal, the input signal indicative of a current generated by one of the one or more nanogap sensors;
   a current conveyor coupled to the readout input to provide current from the readout input without disturbing a measurement of the one or more nanogap sensors;
   a relaxation oscillator, coupled to the current conveyor for oscillating with an oscillation frequency indicative of the input signal; and
   a counter coupled to the relaxation oscillator to count oscillations.

2. The system according to claim 1, wherein the relaxation oscillator is a current-controlled relaxation oscillator for converting the input signal received in an analog form to a digital signal.

3. The system according to claim 1, wherein the relaxation oscillator is configured to transform the input signal into a phase of the relaxation oscillator.

4. The system according to claim 3, wherein the counter configured to determine a number of oscillation cycles of the relaxation oscillator, wherein the number is a digital representation of the input current signal.

5. The system according to claim 4, further comprising:
   a register configured to store a count value of the counter.

6. The system according to claim 4, further comprising:
   an encoder, coupled to an output of the counter, and configured to reduce a data word width of the digital representation based on one or more parameters of the one or more nanogap sensors.

7. The system according to claim 6, further comprising:
   a register, coupled to an output of the encoder, and configured to store a digital value provided at the output of the encoder.

8. The system according to claim 1, further comprising: a plurality of nanogap sensors; and a multiplexer, coupled to the plurality of nanogap sensors and further coupled to the readout input, and configured to provide the input current signal by selecting one of the plurality of nanogap sensors for readout.

9. The system according to claim 8, wherein the multiplexer includes a plurality of transistors, and wherein each individual nanogap sensor of the plurality of nanogap sensors is coupled to a corresponding one of the plurality of transistors.

10. The system according to claim 9, wherein the transistors include metal-oxide- semiconductor field-effect transistors.

11. The system according to claim 10, wherein, for each individual nanogap sensor of the plurality of nanogap sensors, a sense electrode of the individual nanogap sensor is coupled to a source/drain terminal of the corresponding one of the plurality of transistors.

12. The system according to claim 9, wherein:
the plurality of transistors is a first plurality of transistors,
the multiplexer further includes a second plurality of transistors,
each individual nanogap sensor of the plurality of nanogap sensors is further coupled to a corresponding one of the second plurality of transistors, and
during operation of the system, for each individual nanogap sensor of the plurality of nanogap sensors, when the corresponding one of the first plurality of transistors is on, the corresponding one of the second plurality of transistors is off, and vice versa.

13. The system according to claim 12, wherein:
the transistors of the second plurality of transistors include/are metal-oxide-semiconductor field-effect transistors,
for each individual nanogap sensor of the plurality of nanogap sensors, during operation of the system, a sense electrode of the individual nanogap sensor is coupled to a first source/drain (S/D) terminal of the corresponding one of the second plurality of transistors, and a second S/D terminal of the corresponding one of the second plurality of transistors is held at a potential that is substantially equal to a voltage on the sense electrode.

14. The system according to claim 1 wherein, the current conveyor is an active cascode, coupled between the one or more nanogap sensors and the readout input, configured to control voltage across sensor electrodes of the one or more nanogap sensors.

15. The system according to claim 1, further comprising the one or more nanogap sensors.

16. The system according to claim 15, further comprising one or more fluidic channels for providing one or more fluid analytes to the one or more nanogap sensors.

17. The system according to claim 1, wherein:
the one or more nanogap sensors are DNA sensors,
each of the one or more nanogap sensors includes at least a first electrode and a second electrode separated by a nanogap, and
at least one of the first and the second electrodes includes one or more layers of one or more of thiols, di-thiols, or alkanethiols facing the other electrode.

18. A system for the measurement of data acquired by arrays of nanogap sensors, the system comprising:
a plurality of nanogap sensors, the array having a readout signal which is indicative of nanogap sensor current;
a multiplexer, the multiplexer coupled to the plurality of nanogap sensors and further coupled to the readout signal and configured to provide an input current signal to the plurality of nanogap sensors by selecting one of the plurality of nanogap sensors for readout signal;
a relaxation oscillator, the relaxation oscillator coupled to the readout signal;
a counter configured to determine a number of oscillation cycles of the relaxation oscillator, wherein the number is a digital representation of the input current signal; and
logic programmed to identify a base pair based at least on the number of oscillations.

19. The system according to claim 18, wherein the sensor logic is implemented in at least one of hardware, software, and firmware.

20. A method of identifying base pairs from measurement of nanogap sensors, the method comprising:
receiving plurality of currents from a plurality of nanogap sensors;
multiplexing the plurality of currents;
receiving the multiplexed plurality of currents at a relaxation oscillator;
producing a plurality of oscillatory signals based on the multiplexed plurality of currents;
counting a number of oscillations in each of the plurality of oscillatory signal;
storing number of oscillations in each of the plurality of oscillatory signal; and
determining a plurality of base pairs from at the number of oscillations in each of the plurality of oscillatory signal.

* * * * *